US009732356B2

(12) United States Patent
Alam et al.

(10) Patent No.: US 9,732,356 B2
(45) Date of Patent: Aug. 15, 2017

(54) HEPATOCYTE BASED INSULIN GENE THERAPY FOR DIABETES

(71) Applicant: Wisconsin Alumni Research Foundation, Madison, WI (US)

(72) Inventors: Tausif Alam, Madison, WI (US); Hans Sollinger, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 31 days.

(21) Appl. No.: 14/133,016

(22) Filed: Dec. 18, 2013

(65) Prior Publication Data

US 2014/0170123 A1 Jun. 19, 2014

Related U.S. Application Data

(62) Division of application No. 13/490,081, filed on Jun. 6, 2012, now abandoned.

(60) Provisional application No. 61/494,134, filed on Jun. 7, 2011.

(51) Int. Cl.
| | |
|---|---|
| *A61K 35/407* | (2015.01) |
| *C07K 14/62* | (2006.01) |
| *C12N 15/85* | (2006.01) |
| *C12N 15/86* | (2006.01) |
| *A61K 38/00* | (2006.01) |

(52) U.S. Cl.
CPC ............ *C12N 15/85* (2013.01); *A61K 35/407* (2013.01); *C07K 14/62* (2013.01); *C12N 15/86* (2013.01); *A61K 38/00* (2013.01); *C12N 2710/10042* (2013.01); *C12N 2830/002* (2013.01); *C12N 2830/15* (2013.01); *C12N 2830/42* (2013.01); *C12N 2840/105* (2013.01)

(58) Field of Classification Search
CPC ...... A61K 35/407; C07K 14/62; C12N 15/85; C12N 15/86; C12N 2710/10041; C12N 2830/15
See application file for complete search history.

(56) References Cited

U.S. PATENT DOCUMENTS

| 5,427,940 | A | 6/1995 | Newgard | |
|---|---|---|---|---|
| 5,534,404 | A | 7/1996 | Laurance et al. | |
| 6,352,857 | B1 | 3/2002 | Alam et al. | |
| 6,933,133 | B2 | 8/2005 | Alam et al. | |
| 7,425,443 | B2 | 9/2008 | Alam et al. | |
| 2005/0265972 | A1* | 12/2005 | Alam | A61K 38/28 424/93.2 |
| 2010/0120152 | A1* | 5/2010 | Wooddell | C07K 14/765 435/455 |

FOREIGN PATENT DOCUMENTS

WO 9219195 A1 11/1992

OTHER PUBLICATIONS

Chen et al, Mol. Ther. 8(3):495-500, 2003.*
Kunstman, Alam and Sollinger, Abstract P100, "Hepatocyte-based Gene Therapy for Type 1 Diabetes Mellitus", J. Surg. Res. 137(2): p. 277, Feb. 2007; oral poster presentation Wednesday, Feb. 7, 2007.*
Sollinger, Alam, Held and Forsberg, Abstract 308, "Hepatocyte-based Insulin Gene Therapy", Transplantation 86(2S): pp. 109-110, Jul. 27, 2008; oral poster presentation Tuesday, Jul. 29, 2008.*
Kunstman, Alam and Sollinger, Abstract P100, "Hepatocyte-based Gene Therapy for Type 1 Diabetes Mellitus", J. Surg. Res. 137(2):p. 277, Feb. 2007; oral poster presentation Wednesday, Feb. 7.*
Sollinger, Alam, Held and Forsberg, Abstract 308, "Hepatocyte-based Insulin Gene Therapy", Transplantation 86(2S):pp. 109-110, Jul. 27, 2008.*
Alam et al, PLOS ONE 8(6):e67515, 2013.*
Alam, T., Reduction in Diabetic Hyperglycemia by Glucose-Regulated Insulin Release from Transduced Hepatocytes, 2000.
Alam, et al., Glucose-Regulated Insulin Production in Hepatocytes, Transplantation, 2002, 74(12):1781-1787.
Chen, et al., Minicircle DNA Vectors Devoid of Bacterial DNA Result in Persistent and High-Level Transgene in Vivo, Molecular Therapy, 2003, 8(3):495-500 Expression.
Chen, et al., Technical Report—Improved Production and Purification of Minicircle DNA Vector Free of Plasmid Bacterial Sequences and Capable of Persistent Transgene Expression in Vivo, Human Gene Therapy, 2005, 16:126-131.
Groskreutz, et al., Genetically Engineered Proinsulin Constitutively Processed and Secreted as Mature, Active Insulin, Journal of Biological Chemistry, 1994, 269(8):6241-6245.
Hafenrichter, et al., Quantitative Evaluation of Liver-Specific Promoters From Retroviral Vectors After in Vivo Transduction of Hepatocytes, Blood, 1994, 84(10):3394-3404.
Heard, et al., Determinants of Rat Albumin Promoter Tissue Specificity Analyzed by an Improved Transient Expression System, Molecular and Cellular Biology, 1987, 7(7):2425-2434.
Heng, et al., Chromatin Loops are Selectively Anchored Using Scaffold/Matrix-Attachment Regions, Journal of Cell Science, 2004, 117:999-1008.
Jin, et al., The Alpha-Fetoprotein Enhancer Region Activates the Albumin and Alpha-Fetoprotein Promoters During Liver Development, Developmental Biology, 2009, 336(2):294-300.
Kay, et al., A Robust System for Production of Minicircle Dna Vectors, Nature Biotechnology, 2010, 28(12):1287-1289.

(Continued)

*Primary Examiner* — Kevin Hill
(74) *Attorney, Agent, or Firm* — Quarles & Brady LLP

(57) ABSTRACT

A method and vectors for controlling blood glucose levels in a mammal are disclosed. In one embodiment, the method comprises the steps of: treating the hepatocyte cells of a patient with a first, second or third vector, wherein the first vector comprises a promoter enhancer, glucose inducible regulatory elements, a liver-specific promoter, a gene encoding human insulin with modified peptidase and an albumin 3'UTR and lacks an HGH intron, wherein the second vector comprises an HGH intron, glucose inducible regulatory elements, a liver-specific promoter, a gene encoding human insulin with modified peptidase site and an albumin 3'UTR and lacks a promoter enhancer, wherein the third vector comprises an HGH intron, glucose inducible regulatory elements, a liver-specific promoter, a gene encoding human insulin with modified peptidase site, an albumin 3'UTR and a promoter enhancer and observing the patient's insulin levels, wherein the patient's insulin levels are controlled.

21 Claims, 21 Drawing Sheets

(56) References Cited

OTHER PUBLICATIONS

Kwok, et al., Cloning and Nucleotide Sequence Analysis of the Dog Insulin Gene, Journal of Biological Chemistry, 1983, 258(4):2357-2363.
Lacy, et al., Islet Transplantation in Treating Diabetes, Annual Review of Medicine, 1986, 37:33-40.
Lufino, et al., An S/MAR-Based Infectious Episomal Genomic DNA Expression Vector Provides Long-Term Regulated Functional Complementation of LDLR Deficiency, Nucleic Acids Research, 2007, 35(15):e98, 10 pages.
Samson, S.L., et al., Gene Therapy for Diabetes: Reinventing the Islet; Trends in Endocrinology and Metabolism, vol. 17 No. 3 Apr. 2006; Elsevier.
Sebestyen, et al., Progress Toward a Non-Viral Gene Therapy Protocol for the Treatment of Anemia, Human Gene Therapy, 2007, 18(3):269-285.
Shih, et al., Definition of the Carbohydrate Response Element of the Rat S14 Gene, Journal of Biological Chemistry, 1994, 269(12):9380-9387.
Simonson, et al., Synthesis and Processing of Genetically Modified Human Proinsulin by Rat Myoblast Primary Cultures, Human Gene Therapy, 1996, 7(1):71-78.
Si-Tayeb, et al., Highly Efficient Generation of Human Hepatocyte-Like Cells from Induced Pluripotent Stem Cells, Hepatology, 2010, 51:297-305.
Tuduri', E. et al., Restoring Insulin Production for Type 1 Diabetes; Journal of Diabetes, 4 (2012) 319-331; doi: 10.1111/j.1753-0407.2012.00196.x Wiley Publishing Asia Pty Ltd.
Valera, et al., Regulated Expression of Human Insulin in the Liver of Transgenic Mice Corrects Diabetic Alterations, Faseb J., 1994, 8:440-447.
Wong, M.S. et al., Gene Therapy in Diabetes; Self/Nonself 1:3; 165-175; Jul./Aug./Sep. 2010.
Wong, et al., Non-Viral S/MAR Vectors Replicate Episomally in Vivo When Provided with a Selective Advantage, Gene Therapy, 2011, 18:82-87.
Wooddell, et al., Sustained Liver-Specific Transgene Expression from the Albumin Promoter in Mice Following Hydrodynamic Plasmid DNA Delivery, Journal of Gene Medicine, 2008, 10(5):551-563.
Wooddell, et al., Dose Response in Rodents and Nonhuman Primates After Hydrodynamic Limb Vein Delivery of Naked Plasmid DNA, Human Gene Therapy, 2011, 22(7):889-903.
Zhang, et al., Expression of Naked Plasmid DNA Injected into the Afferent and Efferent Vessels of Rodent and Dog Livers, Human Gene Therapy, 1997, 8(15)1763-1772.
Zhang, et al., Naked DNA Gene Transfer in Mammalian Cells, Methods in Molecular Biology, 2004, 245:251-264.
International Bureau of WIPO, International Preliminary Report on Patentability, issued Dec. 10, 2013 in the matter of PCT/US2012/041099.
Sanlioglu, et al.: "Insulin Gene Therapy from Design to Beta Cell Generation", Expert Reviews in Molecular Medicine, Cambridge University Press, Inc., vol. 14; Oct. 2012; e18; DOI: 10.1017/erm 2012.12—the whole document.
Simpson, et al.: "Long Term Reversal of Diabetes in Non-Obese Diabetic Mice by Liver-Directed Gene Therapy," The Journal of Gene Medicine; Wiley & Sons Online Library, vol. 15; p. 28-41, 2013; DOI: 10.1002/jgm2692—the whole document.
Sollinger, et al.: "Non-Viral Plasmid Based Glucose-Responsive Insulin Gene Thereapy Rescues Hyperglycemia and Weight Loss in Streptozocin-Induced Diabetic Rats"; Central Surgical Association 69th Annual Meeting 2012; Madison, WI, Mar. 1, 2012.
Zhang X. et al., Regional Hydrodynamic gene delivery to the rat liver with physiological volumes of DNA solution. J. Gene Med. 2004; 6(6):693-703.
Kunstman, et al.: "P100", Journal of Surgical Research, Academic Press Inc., San Diego, CA, US, vol. 137, No. 2, Jan. 25, 20707 (Jan. 25, 2007), p. 277, XP005854396, ISSN: 0022-4804, DOI: 10.1016/J.JSS.2006.12.329—the whole document.
Thule, P.M., et al.: "Glucose Regulated Production of Human Insulin in Rat Hepatocytes", Gene Therapy, Macmillan Press Ltd., Basingstoke, GB, vol. 7, No. 3, Feb. 1, 2000 (Feb. 1, 2000), pp. 205-214, XP001057163, ISSN: 0969-7128, DOI: 10.1038/SJ.GT. 3301076—the whole document.
Zhang, C., et al.: "Targeted Minicircle DNA Delivery Using Folate-poly(ethylene glycol)-Polyethylenimine as Non-viral Carrier", Biomaterials, Elsevier Science Publishers BV., Barking, GB, vol. 31, No. 23, Aug. 1, 2010 (Aug. 1, 2010), pp. 6075-6086, XP027089516, ISSN: 0142-9612 [retrieved on May 20, 2010]—the whole document.
International Search Report; in re PCT/US2012/041099 dated Nov. 5, 2012.
Kunstman, Alam, and Sollinger, Abstract P100, "Hepatocyte-based Gene Therapy for Type 1 Diabetes Mellitus," J. Surg. Res. 137(2), p. 227, Feb. 2007.
Sollinger, Alam, Held, and Forsberg, Abstract 308, "Hepatocyte-based Insulin Gene Therapy," Transplantation 86(2S), p. 109-110, Jul. 27, 2008.

\* cited by examiner

TA1 Expression Cassette (SEQ ID NO: 1)

```
CCGCCCCCTTCACCAAGATCTTTTTGATGGCAGAGTTCAGTTTACCGGGTCACATTGTACCTGGGAAGATT
CAAGGATTTATGGAAAAAGTCAACAACAGGAGTCAGAGCAGCCGGAAAAGCATGGACTCTGTACTTAGGAC
TGCGCTTTGAGCAATGGCACAGCAAGCTTTAACCCTGTTTGCAGTCAGCACACAAACTGTGGTTCAAAGCT
CCACTTTATCTCTTCTTGTGGAATTCagatatcagatcagtttaaAccttgcGGCCGCCAGTTCTCACGTG
GTGGCCACGTGCTTGGGCACGCCAGTTCTCACGTGGTGGCCACGTGCTTGGGCACGAATTCCAGTTCTCAC
GTGGTGGCCACGTGCTTGGGCACTctagtgctcaaatgggagacaaagagattaagctctTatgtaaaatt
tgctgttttacataactttaatgaatggacaaagtcttgTgcatgggggtggggtggggttagagggaa
cagctccagatggcaaacatacgcaagggatttagtcaaacaacttttggcaaagatggtatgatttTgt
aatggggtaggaaccaatgaaatgcgaggtaagtatggttaataatcTacagttattggttaaagaagtat
attagagcgagtctttctgcacacagAtcaccttcctatcaacccactagcctctggcaaaggtacCagc
gcagaGgcttggggcagccgagcggcagccaggccccggcccgggcctcggttccAgaagggagaggagcc
cgccaaggcgcgcaagagagcgggctgcctcgcaGtccgagccggagagggagcgcgagccgcgccggcc
cggacggcctccgaaaccATGGCCCTGTGGATGCGCCTCCTGCCCCTGCTGGCGCTGCTGGCCCTCTGGGG
ACCTGACCCAGCCGCAGCCTTTGTGAACCAACACCTGTGCGGCTCACACCTGGTGGAAGCTCTCTACCTAG
TGTGCGGGGAACGAGGCTTCTTCTACACACCCAgGACCaagCGGGAGGCAGAGGACCTGCAGGTGGGGCAG
GTGGAGCTGGGCGGGGCCCTGGTGCAGGCAGCCTGCAGCCCTTGGCCCTGGAGGGGTCCCGGCAGAAGCG
TGGCATTGTGGAACAATGCTGTACCAGCATCTGCTCCCTCTACCAGCTGGAGAACTACTGCAACTAGACGC
AGCCTGCAGGCAGCGTCGAGTAACATCACATTTAAAAGCATCTCAGGTAACTATATTTTGAATTTTTTAAA
AAAGTAACTATAATAGTTATTATTAAAATAGCAAAGATTGACCATTTCCAAGAGCCATATAGACCAGCACC
GACCACTATTCTAAACTATTTATGTATGTAAATATTAGCTTTTAAAATTCTCAAAATAGTTGCTGAGTTGG
GAACCACTATTATTTCTATCGATTCAGCAGCCGTAAGTCTAGGACAGGCTTAAATTGTTTTCACTGGTGTA
AATTGCAGAAAGATGATCTAAGTAATTTGGCATTTATTTTAATAGGTTTGAAAAACACATGCCATTTTACA
AATAAGACTTATATTTGTCCTTTTGTTTTTCAGCCTACCATGAGAATAAGAGAAAGAAAATGAAGATCAAA
AGCTTATTCATCTGTTTTTCTTTTTCGTTGGTGTAAAGCCAACACCCTGTCTAAAAAACATAAATTTCTTT
AATCATTTTGCCTCTTTTCTCTGTGCTTCAATTAATAAAAATGGAAAGAATCTAATAGAGTGGTACAGCA
CTGTTATTTTTCAAAGATGTGTTGCTATCCTGAAAATTCTGTAGGTTCTGTGGAAGTTCCAGTGTTCTCTC
TTATTCCACTTCGGTAGAGGATTTCTAGTTTCTTGTGGGCTAATTAAATAAATCATTAATACTCTTCTAAG
TTATGGATTATAAACATTCAAAATAATATTTTGACATTATGATAATTCTGAATAAAAGAACAAAAACCATG
GTATAGGTAAGGAATATAAAACATGGCTTTTACCTTAGAAAAAACAATTCTAAAATTCATATGGAATCAAA
AAAGAGCCTGCAAGGGTG
```

Alpha fetoprotein enhancer: AAGAT...ttgc

Figure 6

GIRE: CACGTGGTGGC....CACGTG

Albumin promoter: ctcaaa...ggtacc

Translational enhancer from VEGF: Cag...aaacc

Coding sequence of human insulin gene with mutations for furin compatibility: ATG...TAG 3' untranslated region of human albumin: sequence be TA4 Expression Cassette (SEQ ID NO: 2)

CCGCCCCCTTcaccCATGGCTCGACAGATCgcGGCCGCCAGTTCTCACGTGGTGGCCACGTGCTTGGGCAC
GCCAGTTCTCACGTGGTGGCCACGTGCTTGGGCACGAATTCCAGTTCTCACGTGGTGGCCACGTGCTTGGG
CACTctagtgctcaaatgggagacaaagagattaagctctTatgtaaaatttgctgttttacataacttta
atgaatggacaaagtcttgTgcatgggggtgggggtggggttagaggggaacagctccagatggcaaacat
acgcaagggatttagtcaaacaacttttttggcaaagatggtatgatttTgtaatggggtaggaaccaatga
aatgcgaggtaagtatggttaataatcTacagttattggttaaagaagtatattagagcgagtctttctgc
acacagAtcaccttcctatcaaccccactagcctctggcaaaggtaccTTCGAACAGGTAAGCGCCCCTAA
AATCCCTTTGGCACAATGTGTCCTGAGGGGAGAGGCAGCGACCTGTAGATGGGACGGGGGCACTAACCCTC
AGGGTTTGGGGTTCTGAATGTGAGTATCGCCATCTAAGCCCAGTATTTGGCCAATCTCAGAAAGCTCCTGG
CTCCCTGGAGGATGGAGAGAGAAAAACAAACAGCTCCTGGAGCAGGGAGAGTGTTGGCCTCTTGCTCTCCG
GCTCCCTCTGTTGCCCTCTGGTTTCTCCCCAGGTTCGAAggtaccagcgcagaGgcttggggcagccgagc
ggcagccaggccccggcccgggcctcggttccAgaagggagaggagcccgccaaggcgcgcaagagagcgg
gctgcctcgcaGtccgagccggagagggagcgcgagccgcgccggccccggacggcctccgaaaccATGGC
CCTGTGGATGCGCCTCCTGCCCCTGCTGGCGCTGCTGGCCCTCTGGGGACCTGACCCAGCCGCAGCCTTTG
TGAACCAACACCTGTGCGGCTCACACCTGGTGGAAGCTCTCTACCTAGTGTGCGGGGAACGAGGCTTCTTC
TACACACCCAAgGACCaagCGGGAGGCAGAGGACCTGCAGGTGGGGCAGGTGGAGCTGGGCGGGGGCCCTGG
TGCAGGCAGCCTGCAGCCCTTGGCCCTGGAGGGGTCCCGGCAGAAGCGTGGCATTGTGGAACAATGCTGTA
CCAGCATCTGCTCCCTCTACCAGCTGGAGAACTACTGCAACTAGACGCAGCCTGCAGGCAGCGTCGAGTAA
CATCACATTTAAAAGCATCTCAGGTAACTATATTTTGAATTTTTTAAAAAAGTAACTATAATAGTTATTAT
TAAAATAGCAAAGATTGACCATTTCCAAGAGCCATATAGACCAGCACCGACCACTATTCTAAACTATTTAT
GTATGTAAATATTAGCTTTTAAAATTCTCAAAATAGTTGCTGAGTTGGGAACCACTATTATTTCTATCGAT
TCAGCAGCCGTAAGTCTAGGACAGGCTTAAATTGTTTTCACTGGTGTAAATTGCAGAAAGATGATCTAAGT
AATTTGGCATTTATTTTAATAGGTTTGAAAAACACATGCCATTTTACAAATAAGACTTATATTTGTCCTTT
TGTTTTTCAGCCTACCATGAGAATAAGAGAAAGAAAATGAAGATCAAAAGCTTATTCATCTGTTTTTCTTT
TTCGTTGGTGTAAAGCCAACACCCTGTCTAAAAAACATAAATTTCTTTAATCATTTTGCCTCTTTTCTCTG
TGCTTCAATTAATAAAAAATGGAAAGAATCTAATAGAGTGGTACAGCACTGTTATTTTTCAAAGATGTGTT
GCTATCCTGAAAATTCTGTAGGTTCTGTGGAAGTTCCAGTGTTCTCTCTTATTCCACTTCGGTAGAGGATT
TCTAGTTTCTTGTGGGCTAATTAAATAAATCATTAATACTCTTCTAAGTTATGGATTATAAACATTCAAAA
TAATATTTTGACATTATGATAATTCTGAATAAAAGAACAAAAACCATGGTATAGGTAAGGAATATAAAACA
TGGCTTTTACCTTAGAAAAAACAATTCTAAAATTCATATGGAATCAAAAAAGAGCCTGCaAGGGGTG

Figure 7

GIRE: CACGTGGTGGC....CACGTG

Albumin promoter: ctcaaa...ggtacc

Human growth hormone intron: TTCG...ggtac

Translational enhancer from VEGF: Cag...aaacc

Coding sequence of human insulin gene with mutations for furin compatibility: ATG....TAG 3' untranslated region of human albumin: sequence beyond end codon TAG

Figure 7 (continued)

TA2 Expression Cassette   (SEQ ID NO:3)

CCGCCCCCTTcaccAAGATCTTTTTGATGGCAGAGTTCAGTTTACCGGGTCACATTGTACCTGGGAAGATT
CAAGGATTTATGGAAAAAGTCAACAACAGGAGTCAGAGCAGCCGGAAAAGCATGGACTCTGTACTTAGGAC
TGCGCTTTGAGCAATGGCACAGCAAGCTTTAACCCTGTTTGCAGTCAGCACACAAACTGTGGTTCAAAGCT
CCACTTTATCTCTTCTTGTGGAATTCagatatcagatcagtttaaAccttgcGGCCGCCAGTTCTCACGTG
GTGGCCACGTGCTTGGGCACGCCAGTTCTCACGTGGTGGCCACGTGCTTGGGCACGAATTCCAGTTCTCAC
GTGGTGGCCACGTGCTTGGGCACTctagtgctcaaatgggagacaaagagattaagctctTatgtaaaatt
tgctgttttacataactttaatgaatggacaaagtcttgTgcatggggggtggggtggggttagagggggaa
cagctccagatggcaaacatacgcaagggatttagtcaaacaacttttttggcaaagatggtatgattTgt
aatggggtaggaaccaatgaaatgcgaggtaagtatggttaataatcTacagttattggttaaagaagtat
attagagcgagtctttctgcacacagAtcaccttcctatcaacccactagcctctggcaaaggtaccTTC
GAACAGGTAAGCGCCCCTAAAATCCCTTTGGCACAATGTGTCCTGAGGGGAGAGGCAGCGACCTGTAGATG
GGACGGGGGCACTAACCCTCAGGGTTTGGGGTTCTGAATGTGAGTATCGCCATCTAAGCCCAGTATTTGGC
CAATCTCAGAAAGCTCCTGGCTCCCTGGAGGATGGAGAGAGAAAAACAAACAGCTCCTGGAGCAGGGAGAG
TGTTGGCCTCTTGCTCTCCGGCTCCCTCTGTTGCCCTCGGTTTCTCCCCAGGTTCGAAggtaccagcgca
gaGgcttggggcagccgagcggcagccaggccccggcccgggcctcggttccAgaagggagaggagcccgc
caaggcgcgcaagagagcgggctgcctcgcaGtccgagccggagagggagcgcgagccgcgccggccccgg
acggcctccgaaaccATGGCCCTGTGGATGCGCCTCCTGCCCCTGCTGGCGCTGCTGGCCCTCTGGGGACC
TGACCCAGCCGCAGCCTTTGTGAACCAACACCTGTGCGGCTCACACCTGGTGGAAGCTCTCTACCTAGTGT
GCGGGGAACGAGGCTTCTTCTACACACCCAAGACCaagCGGGAGGCAGAGGACCTGCAGGTGGGGCAGGTG
GAGCTGGGCGGGGGCCCTGGTGCAGGCAGCCTGCAGCCCTTGGCCCTGGAGGGGTCCCGGCAGAAGCGTGG
CATTGTGGAACAATGCTGTACCAGCATCTGCTCCCTCTACCAGCTGGAGAACTACTGCAACTAGACGCAGC
CTGCAGGCAGCGTCGAGTAACATCACATTTAAAAGCATCTCAGGTAACTATATTTTGAATTTTTTAAAAAA
GTAACTATAATAGTTATTATTAAAATAGCAAAGATTGACCATTTCCAAGAGCCATATAGACCAGCACCGAC
CACTATTCTAAACTATTTATGTATGTAAATATTAGCTTTTAAAATTCTCAAAATAGTTGCTGAGTTGGGAA
CCACTATTATTTCTATCGATTCAGCAGCCGTAAGTCTAGGACAGGCTTAAATTGTTTTCACTGGTGTAAAT
TGCAGAAAGATGATCTAAGTAATTTGGCATTTATTTTAATAGGTTTGAAAAACACATGCCATTTTACAAAT
AAGACTTATATTTGTCCTTTTGTTTTTCAGCCTACCATGAGAATAAGAGAAAGAAAATGAAGATCAAAAGC
TTATTCATCTGTTTTTCTTTTTCGTTGGTGTAAAGCCAACACCCTGTCTAAAAAACATAAATTTCTTTAAT
CATTTTGCCTCTTTTCTCTGTGCTTCAATTAATAAAAATGGAAAGAATCTAATAGAGTGGTACAGCACTG
TTATTTTTCAAAGATGTGTTGCTATCCTGAAAATTCTGTAGGTTCTGTGGAAGTTCCAGTGTTCTCTCTTA
TTCCACTTCGGTAGAGGATTTCTAGTTTCTTGTGGGCTAATTAAATAAATCATTAATACTCTTCTAAGTTA
TGGATTATAAACATTCAAAATAATATTTTGACATTATGATAATTCTGAATAAAAGAACAAAAACCATGGTA
TAGGTAAGGAATATAAAACATGGCTTTTACCTTAGAAAAAACAATTCTAAAATTCATATGGAATCAAAAAA
GAGCCTGCaAGGGTG

Figure 11

Alpha fetoprotein enhancer: AAGAT...ttgc

GIRE: CACGTGGTGGC....CACGTG

Albumin promoter: ctcaaa...ggtacc

Human growth hormone intron: TTCG...ggtac

Translational enhancer from VEGF: Cag...aaacc

Coding sequence of human insulin gene with mutations for furin compatibility: ATG...TAG 3' untranslated region of human albumin: sequence beyond end codon TAG Figure 11 (continued)

Human Insulin in Serum of Diabetic Rats Treated With Plasmid or Minicircle DNA

| Insulin Construct | Insulin (mU/l) (Mean ± S.D.) |
|---|---|
| TA1 Minicircle | 22.1 |
| TA1/SMAR Minicircle | 36.5 ± 21.1 |
| pTED110 | 12.4 ± 10.8 |
| TA1/pENTR | 1.3 ± 0.2 |
| STZ-diabetic | 0.4 ± 0.2 |
| Normal Control | 0.6 ± 0.6 |

Figure 15

Glucose-dependent Insulin Production From Human Stem Cells Derived Hepatocytes

| Hepatocyte Derivation | Human Insulin ng/day/cm² (Mean ± S.D.) | | Increase in Insulin in High Glucose (High/low) |
|---|---|---|---|
| | High Glucose | Low Glucose | |
| hES Cells | 266 ± 48 | 61 ± 34 | 4.4 |
| iPS Cells | 121 ± 8 | 12 ± 5 | 10.1 |
| Normal Rats | 88 ± 15 | 11 ± 1 | 8.0 |

Figure 17

SEQUENCE LISTING

<160> NUMBER OF SEQ ID NOS: 3

<210> SEQ ID NO 1
<211> LENGTH: 2077
<212> TYPE: DNA
<213> ORGANISM: Artificial Sequence
<220> FEATURE:
<223> OTHER INFORMATION: rats

<400> SEQUENCE: 1
ccgcccsctt caccaagatc tttttgatgg cagagttcag tttaccgggt cacattgtac    60

```
ctgggaagat tcaaggattt atggaaaaag tcaacaacag gagtcagagc agccggaaaa    120
gcatggactc tgtacttagg actgcgcttt gagcaatggc acagcaagct ttaaccctgt    180
ttgcagtcag cacacaaact gtggttcaaa gctccacttt atctcttctt gtggaattca    240
gatatcagat cagtttaaac cttgcggccg ccagttctca cgtggtggcc acgtgcttgg    300
gcacgccagt tctcacgtgg tggccacgtg cttgggcacg aattccagtt ctcacgtggt    360
ggccacgtgc ttgggcactc tagtgctcaa atgggagaca aagagattaa gctcttatgt    420
aaaatttgct gttttacata actttaatga atggacaaag tcttgtgcat gggggtgggg    480
gtggggttag aggggaacag ctccagatgg caaacatacg caagggattt agtcaaacaa    540 cttttttggca agatggtat gattttgtaa tggggtagga accaatgaaa tgcgaggtaa    600
gtatggttaa taatctacag ttattggtta aagaagtata ttagagcgag tctttctgca    660
cacagatcac cttcctatca accccactag cctctggcaa aggtaccagc gcagaggctt    720
ggggcagccg agcggcagcc aggccccggc ccgggcctcg gttccagaag ggagaggagc    780
ccgccaaggc gcgcaagaga gcgggctgcc tcgcagtccg agccggagag ggagcgcgag    840
ccgcgccggc cccggacggc ctccgaaacc atggccctgt ggatgcgcct cctgcccctg    900
ctggcgctgc tggccctctg ggacctgac ccagccgcag cctttgtgaa ccaacacctg    960
tgcggctcac acctggtgga agctctctac ctagtgtgcg gggaacgagg cttcttctac    1020
acacccagga ccaagcggga ggcagaggac ctgcaggtgg ggcaggtgga gctgggcggg    1080
ggccctggtg caggcagcct gcagcccttg gccctggagg ggtcccggca gaagcgtggc    1140
attgtggaac aatgctgtac cagcatctgc tccctctacc agctggagaa ctactgcaac    1200
tagacgcagc ctgcaggcag cgtcgagtaa catcacattt aaaagcatct caggtaacta    1260
tattttgaat tttttaaaaa agtaactata atagttatta ttaaaatagc aaagattgac    1320
catttccaag agccatatag accagcaccg accactattc taaactattt atgtatgtaa    1380
atattagctt ttaaaattct caaaatagtt gctgagttgg gaaccactat tatttctatc    1440
gattcagcag ccgtaagtct aggacaggct taaattgttt tcactggtgt aaattgcaga    1500
aagatgatct aagtaatttg gcatttattt taataggttt gaaaaacaca tgccatttta    1560
caaataagac ttatatttgt cctttttgttt ttcagcctac catgagaata agagaaagaa    1620
aatgaagatc aaaagcttat tcatctgttt ttcttttcg ttggtgtaaa gccaacaccc    1680
tgtctaaaaa acataaattt ctttaatcat tttgcctctt ttctctgtgc ttcaattaat    1740
aaaaaatgga aagaatctaa tagagtggta cagcactgtt atttttcaaa gatgtgttgc    1800
tatcctgaaa attctgtagg ttctgtggaa gttccagtgt tctctcttat tccacttcgg    1860
tagaggattt ctagtttctt gtgggctaat taaataaatc attaatactc ttctaagtta    1920
tggattataa acattcaaaa taatattttg acattatgat aattctgaat aaaagaacaa    1980
aaaccatggt ataggtaagg aatataaaac atggcttttt acctagaaaa aacaattcta    2040
aaattcatat ggaatcaaaa aagagcctgc aagggtg                              2077
```

<210> SEQ ID NO 2
<211> LENGTH: 2125
<212> TYPE: DNA
<213> ORGANISM: Artificial Sequence
<220> FEATURE:
<223> OTHER INFORMATION: rats

<400> SEQUENCE: 2

```
ccgcccccctt cacccatggc tcgacagatc gcggccgcca gttctcacgt ggtggccacg    60
tgcttgggca cgccagttct cacgtggtgg ccacgtgctt gggcacgaat tccagttctc    120
acgtggtggc cacgtgcttg ggcactctag tgctcaaatg ggagacaaag agattaagct    180
cttatgtaaa atttgctgtt ttacataact ttaatgaatg acaaagtct tgtgcatggg     240 ggtgggggtg gggttagagg ggaacagctc cagatggcaa acatacgcaa gggatttagt    300
caaacaactt tttggcaaag atggtatgat tttgtaatgg ggtaggaacc aatgaaatgc    360
gaggtaagta tggttaataa tctacagtta ttggttaaag aagtatatta gagcgagtct    420
ttctgcacac agatcacctt cctatcaacc ccactagcct ctggcaaagg taccttcgaa    480
caggtaagcg cccctaaaat ccctttggca caatgtgtcc tgaggggaga ggcagcgacc    540
tgtagatggg acgggggcac taaccctcag ggtttgggt tctgaatgtg agtatcgcca     600
tctaagccca gtatttggcc aatctcagaa agctcctggc tccctggagg atggagagag    660
aaaaacaaac agctcctgga gcagggagag tgttggcctc ttgctctccg gctccctctg    720
ttgccctctg gtttctcccc aggttcgaag gtaccagcgc agaggcttgg ggcagccgag    780
cggcagccag gccccggccc gggcctcggt tccagaaggg agaggagccc gccaaggcgc    840
gcaagagagc gggctgcctc gcagtccgag ccggagaggg agcgcgagcc gcgccggccc    900
cggacggcct ccgaaaccat ggccctgtgg atgcgcctcc tgcccctgct ggcgctgctg    960
gccctctggg gacctgaccc agccgcagcc tttgtgaacc aacacctgtg cggctcacac    1020
ctggtggaag ctctctacct agtgtgcggg gaacgaggct tcttctacac acccaggacc    1080
aagcgggagg cagaggacct gcaggtgggg caggtggagc tgggcggggg ccctggtgca    1140
ggcagcctgc agcccttggc cctggagggg tcccggcaga agcgtggcat tgtggaacaa    1200
tgctgtacca gcatctgctc cctctaccag ctggagaact actgcaacta gacgcagcct    1260
gcaggcagcg tcgagtaaca tcacatttaa aagcatctca ggtaactata ttttgaattt    1320
tttaaaaaag taactataat agttattatt aaaatagcaa agattgacca tttccaagag    1380
ccatatagac cagcaccgac cactattcta aactatttat gtatgtaaat attagctttt    1440
aaaattctca aaatagttgc tgagttggga accactatta tttctatcga ttcagcagcc    1500
gtaagtctag gacaggctta aattgttttc actggtgtaa attgcagaaa gatgatctaa    1560
gtaatttggc atttatttta ataggtttga aaaacacatg ccattttaca aataagactt    1620
atatttgtcc ttttgttttt cagcctacca tgagaataag agaaagaaaa tgaagatcaa    1680
aagcttattc atctgttttt ctttttcgtt ggtgtaaagc caacaccctg tctaaaaaac    1740
ataaatttct ttaatcattt tgcctctttt ctctgtgctt caattaataa aaaatggaaa    1800
gaatctaata gagtggtaca gcactgttat ttttcaaaga tgtgttgcta tcctgaaaat    1860
tctgtaggtt ctgtggaagt tccagtgttc tctcttattc cacttcggta gaggatttct    1920
agtttcttgt gggctaatta aataaatcat taatactctt ctaagttatg gattataaac    1980
attcaaaata atattttgac attatgataa ttctgaataa aagaacaaaa accatggtat    2040
aggtaaggaa tataaaacat ggcttttacc ttagaaaaaa caattctaaa attcatatgg    2100
aatcaaaaaa gagcctgcaa gggtg                                         2125
```

<210> SEQ ID NO 3
<211> LENGTH: 2358
<212> TYPE: DNA
<213> ORGANISM: Artificial Sequence
<220> FEATURE:
<223> OTHER INFORMATION: rats

<400> SEQUENCE: 3

```
ccgcccctt caccaagatc tttttgatgg cagagttcag tttaccgggt cacattgtac    60
ctgggaagat tcaaggattt atggaaaaag tcaacaacag gagtcagagc agccggaaaa   120
gcatggactc tgtacttagg actgcgcttt gagcaatggc acagcaagct ttaaccctgt   180
ttgcagtcag cacacaaact gtggttcaaa gctccacttt atctcttctt gtggaattca   240
gatatcagat cagtttaaac cttgcggccg ccagttctca cgtggtggcc acgtgcttgg   300
gcacgccagt tctcacgtgg tggccacgtg cttgggcacg aattccagtt ctcacgtggt   360
ggccacgtgc ttgggcactc tagtgctcaa atgggagaca aagagattaa gctcttatgt   420
aaaatttgct gttttacata actttaatga atggacaaag tcttgtgcat ggggtgggg    480
gtggggttag agggaacag ctccagatgg caaacatacg caagggattt agtcaaacaa    540
cttttggca aagatggtat gattttgtaa tggggtagga accaatgaaa tgcgaggtaa    600
gtatggttaa taatctacag ttattggtta aagaagtata ttagagcgag tctttctgca   660
cacagatcac cttcctatca accccactag cctctggcaa aggtaccttc gaacaggtaa   720
gcgcccctaa aatccctttg gcacaatgtg tcctgagggg agaggcagcg acctgtagat   780
gggacgggg cactaaccct cagggtttgg ggttctgaat gtgagtatcg ccatctaagc    840
ccagtatttg gccaatctca gaaagctcct ggctccctgg aggatggaga gagaaaaaca   900
aacagctcct ggagcaggga gagtgttggc ctcttgctct ccggctccct ctgttgccct   960
ctggtttctc cccaggttcg aaggtaccag cgcagaggct tggggcagcc gagcggcagc  1020
caggccccgg cccgggcctc ggttccagaa gggagaggag cccgccaagg cgcgcaagag  1080
agcgggctgc ctcgcagtcc gagccggaga gggagcgcga gccgcgccgg ccccggacgg  1140
cctccgaaac catggccctg tggatgcgcc tcctgcccct gctggcgctg ctggcccttc  1200
ggggacctga cccagccgca gccttttgtga accaacacct gtgcggctca cacctggtgg  1260
aagctctcta cctagtgtgc ggggaacgag gcttcttcta cacacccagg accaagcggg  1320
aggcagagga cctgcaggtg gggcaggtgg agctgggcgg gggccctggt gcaggcagcc  1380
tgcagccctt ggccctggag gggtcccggc agaagcgtgg cattgtggaa caatgctgta  1440
ccagcatctg ctcctctac cagctggaga actactgcaa ctagacgcag cctgcaggca  1500
gcgtcgagta acatcacatt taaaagcatc tcaggtaact atatttgaa ttttttaaaa   1560
aagtaactat aatagttatt attaaaatag caaagattga ccatttccaa gagccatata   1620
gaccagcacc gaccactatt ctaaactatt tatgtatgta aatattagct tttaaaattc   1680
tcaaaatagt tgctgagttg ggaaccacta ttatttctat cgattcagca gccgtaagtc   1740
taggacaggc ttaaattgtt ttcactggtg taaattgcag aaagatgatc taagtaattt   1800
ggcatttatt ttataggtt tgaaaaacac atgccatttt acaataaga cttatattg     1860
tccttttgtt tttcagccta ccatgagaat aagagaaaga aatgaagat caaaagctta    1920
ttcatctgtt tttcttttc gttggtgtaa agccaacacc ctgtctaaaa aacataaatt    1980
tctttaatca ttttgcctct tttctctgtg cttcaattaa taaaaatgg aaagaatcta    2040
atagagtggt acagcactgt tattttcaa agatgtgttg ctatcctgaa aattctgtag    2100
gttctgtgga agttccagtg ttctctctta ttccacttcg gtagaggatt tctagtttct   2160
tgtgggctaa ttaaataaat cattaatact cttctaagtt atggattata acattcaaa    2220
ataatatttt gacattatga taattctgaa taaaagaaca aaaaccatgg tataggtaag   2280
```

```
gaatataaaa catggctttt accttagaaa aaacaattct aaaattcata tggaatcaaa    2340
aaagagcctg caagggtg                                                  2358
```

HEPATOCYTE BASED INSULIN GENE THERAPY FOR DIABETES

CROSS-REFERENCE TO RELATED APPLICATION

This application is a divisional application of U.S. application Ser. No. 13/490,081 filed on Jun. 6, 2012, claims priority to U.S. Provisional Application Ser. No. 61/494,134, filed Jun. 7, 2011, both of which are incorporated herein by reference in their entirety.

STATEMENT REGARDING FEDERALLY SPONSORED RESEARCH OR DEVELOPMENT

N/A

BACKGROUND

This invention relates to treatment of diabetes using hepatocyte-based therapy, and specifically to a method of utilizing hepatocyte cells comprising a genetic construct that has a coding sequence for a proinsulin expressible in the cells in response to glucose levels. The proinsulin synthesized in the cells is further processed into a secretable, active insulin.

Insulin is normally produced in and secreted by the beta cells of the islets of Langerhans in the pancreas. Mature insulin is a protein having two polypeptide chains, A and B, held together by disulfide bonds. The glucose responsive release of insulin from the beta cells is a complex event including gene expression, posttranslational modification and secretion. The initial protein product and insulin precursor is preproinsulin, a single polypeptide chain having an N-terminal signal sequence and an intervening sequence, the C-peptide, between the B and A chains. The signal sequence is cleaved during transport from the rough endoplasmic reticulum to form proinsulin. The proinsulin is packaged into secretory granules along with specific enzymes required for its processing. Proinsulin folds into a specific three-dimensional structure, forming disulfide bonds. Mature insulin results from removal of the C-peptide. In beta cells, this function is catalyzed by endopeptidases that recognize the specific amino acid sequences at the junction of the B chain and the C peptide (B-C junction) and at the junction of the C chain and the A peptide (C-A junction). Mature insulin, stored in secretory granules, is released in response to elevated blood glucose levels. The detailed mechanism of insulin release is not completely understood, but the process involves migration to and fusion of the secretory granules with the plasma membrane prior to release.

In normally functioning beta cells, insulin production and release is affected by the glycolytic flux. Glucokinase and glucose transporter 2 (GLUT-2) are two proteins that are believed to be involved in sensing changes in glucose concentration in beta cells. A reduction in GLUT-2, which is involved in glucose transport, is correlated with decreased expression of insulin; loss of glucokinase activity causes a rapid inhibition of insulin expression.

Autoimmune destruction of pancreatic beta cells causes insulin-dependent diabetes mellitus or Type 1 diabetes. As a consequence of partial or complete loss of beta cells, little or no insulin is secreted by the pancreas. Most cells, with the exception of brain cells, require insulin for the uptake of glucose. Inadequate insulin production causes reduced glucose uptake and elevated blood glucose levels. Both reduced glucose uptake and high blood glucose levels are associated with a number of very serious health problems. In fact, without proper treatment, diabetes can be fatal.

One conventional treatment for diabetes involves periodic administration of injectable exogenous insulin. This method has extended the life expectancy of millions of people with the disease. However, blood glucose levels must be carefully monitored to ensure that the individual receives an appropriate amount of insulin. Too much insulin can cause blood glucose levels to drop to dangerously low levels. Too little insulin will result in elevated blood glucose levels. Even with careful monitoring of blood glucose levels, control of diet, and insulin injections, the health of the vast majority of individuals with diabetes is adversely impacted in some way. Replacement of beta cell function is a treatment modality that may have certain advantages over insulin administration, because insulin would be secreted by cells in response to glucose levels in the microenvironment. One way of replacing beta cell function is by pancreas transplantation, which has met with some success. However, the supply of donors is quite limited, and pancreas transplantation is very costly and too problematic to be made widely available to those in need of beta cell function.

There have been many other proposed alternatives for beta cell replacement, including replacing beta cell function with actual beta cells or other insulin-secreting, pancreas-derived cell lines (Lacy, et al., *Ann. Rev. Med.*, 37:33, 1986). Because the immune system recognizes heterologous cells as foreign, the cells have to be protected from immunoactive cells (e.g., T-cells and macrophages mediating cytolytic processes). One approach to protect heterologous cells is physical immunoisolation; however, immunoisolation itself poses significant problems.

U.S. Pat. No. 5,427,940 issued to Newgard discloses another approach to beta cell replacement. This patent describes an artificial beta cell produced by engineering endocrine cells of the At-T-20 ACTH secreting cells. A stably transfected cell, At-T-20, is obtained by introducing cDNA encoding human insulin and the glucose transporter gene, i.e. the GLUT-2 gene, driven by the constitutive CMV promoter. The cell line already expresses the correct isoform of glucokinase required for glucose responsive expression of the proinsulin gene. Although the cell line is responsive to glucose, it is secretagogue-regulated at concentrations below the normal physiological range. Therefore, use of these cells in an animal would likely cause chronic hypoglycemia; furthermore, these cells are derived from a heterologous source and bear antigens foreign to the recipient host.

U.S. Pat. No. 5,534,404 issued to Laurance et al. discloses another approach to obtaining a cell line in which insulin production is secretagogue-regulated. Subpopulations of beta-TC-6 cells having an increased internal calcium concentration, a property associated with insulin secretion, were selected using a cell sorter. After successive passages, a subpopulation of cells that produce insulin in response to glucose in the physiological range (4-10 mM) was selected, and the cells were encapsulated for therapeutic use in alginate bounded by a PAN/PVC permselective hollow fiber membrane according to the method of Dionne (International Patent application No. PCTIUS92/03327).

Valera, et al., *FASEB Journal*, 8: 440 (1994) describes transgenic mouse hepatocytes expressing insulin under the control of the phosphoenol puruvate carboxy kinase (PEPCK) promoter. The PEPCK promoter is sensitive to the glucagon/insulin ratio and is activated at elevated glucose levels. The PEPCK/insulin chimeric gene was injected into fertilized mouse eggs and offspring were screened for integration of the transgene. In transgene positive mice, under conditions of severe islet destruction by streptozotocin (SZ), the production and secretion of intact insulin by the liver compensated for loss of islet function. Despite these prior art attempts, there is a continuing need for alternative methods to conventional insulin therapy for the treatment of diabetes.

BRIEF SUMMARY OF THE INVENTION

In one embodiment, the present invention is a method for obtaining glucose-regulated expression of insulin ex vivo in hepatocyte cells, wherein the method comprises delivering a first, second or third genetic vector for glucose-regulated synthesis of insulin into an isolated hepatocyte cell wherein glucose-regulated expression of insulin occurs. The first vector comprises a promoter enhancer, 1-5 glucose inducible regulatory elements, a liver-specific promoter, a gene encoding insulin with modified peptidase sites and an albumin 3'UTR and lacks an HGH intron. The second vector comprises an HGH intron, glucose inducible regulatory elements, a liver-specific promoter, a gene encoding insulin with modified peptidase sites and an albumin 3'UTR and lacks a promoter enhancer. The third vector comprises an HGH intron, glucose inducible regulatory elements, a liver-specific promoter, a gene encoding insulin with modified peptidase sites, an albumin 3'UTR and a promoter enhancer.

In one embodiment, the invention comprises the step of transplanting the hepatocytes back into a mammal.

In one embodiment, the genetic vector is delivered by exposing the cells to a virus infective for the cells, wherein the virus comprises the genetic construct, and whereby at least a portion of the cells are infected by the virus under suitable conditions and at a sufficient multiplicity.

In one embodiment the mammal is human and the insulin is human insulin.

In another embodiment, the invention is a vector, as described above, suitable for controlling blood glucose levels.

In another embodiment, the invention is a method of controlling blood glucose levels in a mammal, comprising the steps of treating a mammal with a first, second or third vector, as described above.

In one embodiment of the invention, the mammal's cholesterol level decreases after treatment.

In one embodiment of the invention, the mammal's triglyceride level decreases after treatment.

The method of claim 10 wherein the mammal is a cat or dog.

Other embodiments of the present invention are described in the specification, claims and drawings.

BRIEF DESCRIPTION OF THE DRAWINGS

FIG. 6 is the DNA sequence of the TA1 expression cassette.

FIG. 7 is the DNA sequence of the TA4 expression cassette.

FIG. 11 is the DNA sequence of the TA2 expression cassette.

FIG. 15 is a table of human insulin levels in serum of diabetic rats treated with plasmid or minicircle DNA.

FIG. 17 is a table of glucose-dependent insulin production from human stem cells derived from hepatocytes.

DESCRIPTION OF THE INVENTION

In General

Figure 1:
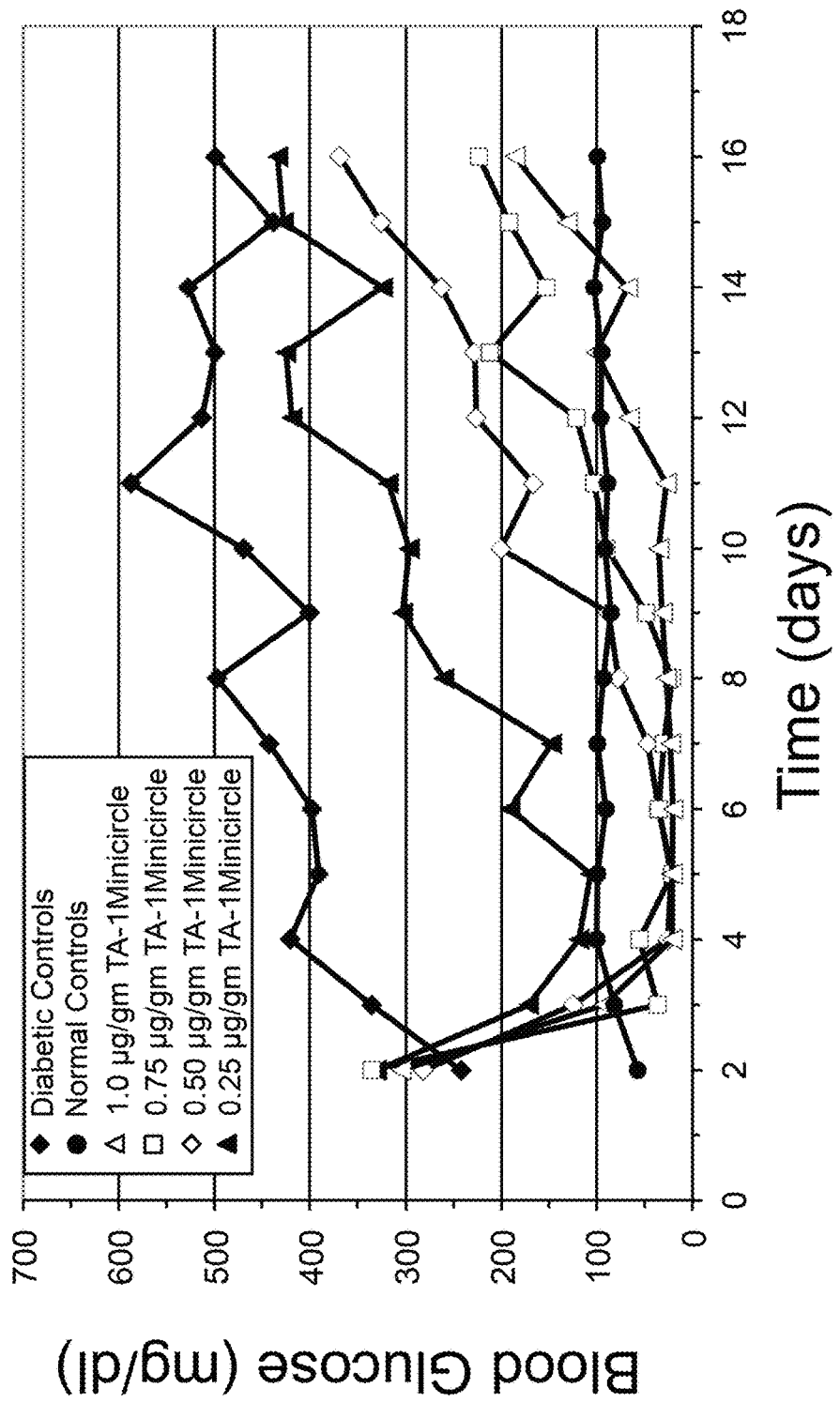
FIG. 1 is a diagram comparing fasting blood glucose versus time in STZ-treated diabetic rats treated with various levels of TA-1M.

Due to a shortage of donor pancreata and the limited long-term success of islet transplants, alternatives for treating Type 1 diabetes (T1D) are needed. We have developed a gene therapy-based glucose regulated hepatic insulin production therapy that demonstrates great promise in treating T1D in experimental animals. Our approach is to apply insulin gene therapy to autologous native hepatocytes or stem cell-derived hepatocytes in an attempt to overcome the two critical shortcomings in treating T1D, which are the shortage of donor organs and the need for life-long use of immunosuppression in transplantation patients.

As the Examples below demonstrate, we examined novel DNA constructs for the ability to improve insulin production. For example, a novel insulin construct (TA1, described below) which contains the human growth hormone (HGH) intron, a translational enhancer, glucose inducible regulatory elements, albumin promoter, human insulin with modified peptidase sites, and the albumin 3'-UTR improved insulin production in cultured hepatocytes and diabetic rats and mice. TA1 resulted in a ~25-fold increase in insulin production from isolated rat hepatocytes compared to our previously published insulin construct [Alam & Sollinger, Transplantation. 2002 Dec. 27; 74(12):178'-7].

In one aspect, the present invention is a novel DNA construct designed to improve insulin production in hepatocytes. Another aspect of the present invention is the creation of hepatocytes with improved insulin production. Another aspect of the present invention is a method of relieving the symptoms of Type I diabetes in a mammalian patient by modulating the production of insulin.

Constructs of the Present Invention

The Examples below demonstrate four insulin constructions containing various elements. The Examples demonstrate that three constructs (TA1, TA2 and TA4) were successful in providing an insulin gene therapy that provides tight control of insulin production. Therefore, the present invention encompasses three types of vector. The first vector type comprises a transcriptional enhancer, glucose inducible regulatory elements, a gene promoter, a translational enhancer, a gene encoding insulin with modified peptidase site and an albumin 3' UTR and lacks an HGH intron. The second vector type comprises an HGH intron, glucose inducible regulatory elements, a gene promoter, a translational enhancer, a gene encoding insulin with modified peptidase site and an albumin 3' UTR and lacks a transcriptional enhancer. The third vector type comprises all of the listed elements.

In another embodiment of the present invention, the constructs of the present invention consist essentially of the elements listed above. By "consist essentially of" we mean that a vector of the present invention will consist of the element described above and possibly other regulatory elements necessary for vector function. For example, plasmids and minicircle vectors may include sequences to facilitate the addition or removal of functional elements, such as restriction sites, or sequences necessary for the replication of the vector itself.

Applicants note that SEQ ID NO: 1, SEQ ID NO: 2 and SEQ ID NO: 3 (FIGS. 6, 7 and 11) are the entire nucleotide sequence of the TA1, TA2 and TA4 expression constructs, respectively. These listings do not include sequences that correspond to minicircle recombination sites, etc. For example, SEQ ID NOs: 1 and 2 do not include specific sequences used for recombination that are found within the commercial minicircle parental plasmid that flank the expression cassettes. Because all these sequences are part of commercial plasmids and readily available, the sequences are not included in the provided information.

SEQ ID NO: 1, SEQ ID NO: 2 and SEQ ID NO:3 include elements that are necessary for the present invention (for example, the elements listed below) and linking and nonessential sequences that are useful for cloning but may be substituted by many other sequences with similar functions.

|  | Residue Location in SEQ ID NO: 1 (TA1) | Residue Location in SEQ ID NO: 2 (TA4) | Residue Location in SEQ ID NO: 3 (TA2) |
|---|---|---|---|
| Alpha fetoprotein (AFP) Enhancer | 15-265 | — | 15-265 |
| Glucose Inducible Regulatory Elements | 279-369 | 46-136 | 279-369 |
| Albumin Promoter Sequence | 380-706 | 147-474 | 380-707 |
| HGH Intron | — | 475-754 | 708-987 |
| VEGF Translational Enhancer | 707-870 | 755-918 | 988-1151 |
| Gene Encoding Human Insulin with Modified B-C and C-A Peptide Junctions for Furin Compatibility | 871-1203 | 919-1251 | 1152-1484 |
| Albumin 3' UTR | 1204-2077 | 1252-2125 | 1485-2358 |

More specifically, the vectors of the present invention comprise the following elements:

Promoter Enhancer

By "promoter enhancer," we preferably mean the alpha-fetoprotein enhancer. The Examples below disclose the use of the alpha-fetoprotein enhancer. This element is designed to enhance transcription of the functionally linked gene sequence encoding a protein in liver cells. Alpha-fetoprotein enhancer increases the effectiveness of albumin promoter and increases the binding of RNA polymerase complex, thereby producing more mRNA, ultimately leading to an increase in protein production. The endogenous factors present in liver cells interact with alpha-fetoprotein enhancer region which activates the albumin and alpha-fetoprotein promoters during liver development and in fully developed liver. Because the effect of AFP enhancer is extinguished in fully developed liver cells through repression of its activity, the region associated with repression is not included in our AFP enhancer sequence, which allows the enhancer activity to persist in fully developed liver cells.

A suitable form of the AFP enhancer of the present invention is disclosed in Jin et al., Developmental Biology 336 (2009) 294-300. A specific sequence of the AFP enhancer can be found at residues 15-265 of SEQ ID NO: 1 (TA1 expression cassette).

In another embodiment of the invention, one would use other promoter enhancers suitable for use with a liver-specific promoter. Many normal promoters are quite large in size and contain multiple regions that modulate transcriptional activity as required for the existing physiological needs at a given time. Therefore, selection of an appropriate promoter enhancer is context dependent. It must work with the promoter in question. If empirical determinations validate functional efficacy of enhancers from other promoters, in conjunction with the liver-specific promoter used, appropriate modifications in insulin expression cassettes can be made to achieve the desired results. Currently, according to the Cold Spring Harbor Laboratory database, there are approximately 400 known regulatory regions and elements that function in liver cells.

Translational Enhancer

By "translational enhancer," we preferably mean the VEGF translational enhancer. The Examples below disclose the use of the VEGF translational enhancer. This element is designed to enhance translation of the functionally linked protein encoding sequence. The VEGF translational enhancer acts as a ribosomal entry site; it increases the effectiveness of the translation process. Thus, its presence causes a larger amount of insulin protein production from a given amount of insulin mRNA.

A specific sequence of the VEGF translational enhancer can be found at residues 707-870 of SEQ ID NO: 1 (TA1 expression cassette) and residues 755-918 of SEQ ID NO: 2 (TA4 expression cassette).

Glucose Inducible Regulatory Elements (GIREs)

The vector of the present invention requires 1-5 GIREs, preferably 2-4 GIREs, most preferably 3 GIREs. One may find the sequence for suitable GIREs at residues 279-369 in SEQ ID NO: 1 and 46-136 in SEQ ID NO: 2. Suitable GIREs are also described below in the Examples and may also be found at U.S. Pat. Nos. 7,425,443 and 6,933,133, both incorporated by reference.

As used herein, a "glucose inducible regulatory element" (GIRE) refers to a polynucleotide sequence containing at least one pair of perfect CACGTG motifs, each member of the pair separated from the other by a sequence of five base pairs. A "glucose responsive regulatory module" contains one or more GIREs. In one example, the regulatory elements were inserted 5' of the 5' untranslated region of the human proinsulin gene and then cloned into an adenovirus vector which was used to transfect hepatocytes. As the Examples below demonstrate, the GIREs provide transcriptional regulation of insulin mRNA in hepatocytes in response to physiologically relevant glucose concentrations.

Promoter Sequence

The constructs of the present invention also involve the use of a gene promoter, preferably an albumin promoter. The albumin promoter is a hepatocyte (liver) specific promoter and is used to ensure that production of insulin is restricted only to liver cells. Therefore, if some of the insulin gene construct ends up in organs other than liver, the construct will not be expressed. Additionally, various components and mechanisms necessary to confer glucose responsiveness to insulin expression using gene constructs of the present invention are endogenous to liver cells. As illustrated in Examples herein, the rat albumin promoter (184 bp), (Heard et al., Determinant of rat albumin promoter tissue specificity analyzed by an improved transient expression system. Mol Cell Biol 1987; 7: 2425) was generated by PCR using rat genomic DNA template, as described previously (Alam et al., Glucose-regulated insulin production in hepatocytes. Transplantation 2002; 74:1781). The use of the rat albumin promoter sequence in the example is provided for illustrative purposes only. Constructs containing an albumin promoter from other species, such as humans, are expected to confer similar properties to the constructs.

One may obtain an albumin promoter by use of primers and PCR amplification after examination of SEQ ID NOs: 1 and 2. The promoter sequence is found at residues 380-706 of SEQ ID NO: 1 and 147-474 of SEQ ID NO: 2 and 380-707 of SEQ ID NO:3.

In principle, any constitutively active liver cell specific promoter capable of sustained moderate to high level transcription can be substituted for albumin promoter. An example of such a promoter is alpha 1-antitrypsin inhibitor (Hafenrichter D G et al. Blood 1994; 84, 3394-404). Currently, according to the Cold Spring Harbor Laboratory database there are approximately 300 known liver specific promoters.

Gene Encoding Insulin with Modified Peptidase Site

The vectors of the present invention comprise a gene encoding insulin, preferably human insulin or non-human mammalian insulin, with a modified peptidase site. The insulin genes of the present invention are also disclosed in SEQ ID NO: 1 at residue 871-1203 and SEQ ID NO: 2 at residue 919-1251.

In one aspect of the invention, one may wish to treat non-human animals. To ensure that no immune reaction to insulin occurs when diabetic animals, such as cats or dogs, are treated using insulin gene therapy, one would use species-specific insulin in minicircle DNA for treating animals. For example, one would use published sequences of insulin for cats and dogs (Kwok et al. 1983 J Biol Chem 258 2357-2363) to generate 3' and 5' primers to amplify the coding sequence of insulin from cDNA preparations made from isolated pancreatic RNA from respective species by standard molecular biology techniques. Alternatively, the coding sequence can also be chemically synthesized. Similarly one may wish to substitute insulin sequences from other animals when treating those animals. These sequences are readily available.

Human insulin cDNA was modified at two junctions of proinsulin where proteolytic processing and maturation of insulin occurs by specific enzymes residing in beta cells but absent in liver cells. The modification at the B and C peptide of human insulin from KTRR to RTKR and at the C and A peptide from LQKR to RQKR makes the two insulin junctions compatible with cleavage specificity of endogenous protease, furin, of liver cells. These modifications are described in the following publications: Simonson G D, Groskreutz C M, Gorman C M, et al. Synthesis and processing of genetically modified human proinsulin by rat myoblast primary cultures. Hum Gene Ther 1996; 7: 71.; Groskreutz D J, Sliwkowski M X, Gorman C M. Genetically engineered pro-insulin constitutively processed and secreted as mature, active insulin. J Biol Chem 1994; 269: 6241.

Regarding the use of non-human insulin, all modifications to the sequence of preproinsulin will be similar in nature to that described for human insulin, wherein the recognition/ processing sites for peptidases found in R-cells (and neuroendocrine tissue) will be changed to sites that can be processed by commonly found proteases in liver (such as furin) and other cells. There are some minor sequence differences in insulin from various species but the key point is to retain the authentic sequence of mature insulin for the given species after processing.

The purpose of the specific mutation is to change the amino acid sequence in such a way that proteolytic processing is possible by commonly found furin. There are multiple codons for several of the amino acids. Theoretically, one can alter the DNA sequence by using an alternative codon but still produce the same polypeptide.

These modifications have been successfully used by Applicants in a published report (Alam T, Sollinger H W. Glucose-regulated insulin production in hepatocytes. Transplantation 2002; 74:1781). An unmodified insulin gene will produce unprocessed proinsulin because the specific enzymes necessary for the maturation by proteolytic processing are absent in liver cells. Proinsulin has minimal biological activity of approximately 100 fold less than the mature insulin.

One may obtain a modified insulin gene by use of primers and PCR amplification with knowledge of the insulin gene in SEQ ID NOs: 1, 2 and 3.

Albumin 3' UTR

The albumin 3' UTR is known to contribute to longevity of the albumin mRNA in hepatocytes. This sequence was obtained from an expression vector plasmid from Mirus (pMIR0375) but this sequence can also be amplified by PCR using reverse transcribed mRNA from liver. The albumin 3' UTR sequence is disclosed in SEQ ID NO: 1 at 1204-2077 and at SEQ ID NO: 2 at residues 1252-2125.

HGH Intron

Two of the constructs of the present invention, TA4 and TA2, comprise the HGH intron. The HGH intron is known to add to the efficiency of mRNA processing and helps in yielding quantitatively more mRNA. There are several other introns, such as beta-globin, that serve similar function to a varying degree. However, the HGH intron is known to function well and is preferred. The HGH intron may be amplified by PCR from the commercially available plasmid pAAV-LacZ [Stratagene, La Jolla, Calif.]. The sequence can also be readily amplified by PCR using genomic DNA as the template. The sequence of the HGH intron is disclosed at residues 475-754 of SEQ ID NO: 2 and 708-987 of SEQ ID NO:3.

Minicircle Embodiment

Optionally, the vector of the present invention is in the "minicircle DNA" format. This is a vector that is virtually devoid of all DNA sequences that are unrelated to expression of insulin. The original minicircle DNA production vector was obtained from the laboratory of Mark Kay, described in the following publications: Chen, Z Y, He, C Y, Ehrhardt, A and Kay, M A (2003). Minicircle DNA vectors devoid of bacterial DNA result in persistent and high-level transgene expression in vivo. Mol Ther 8: 495-500, and Chen Z Y, He C Y, Kay M A (2005) Improved production and purification of minicircle DNA vector free of plasmid bacterial sequence and capable of persistent transgene expression in vivo. Human Gene Ther, 16:126. A newly revised method to easily produce minicircle DNA was published recently (Kay M A, He C, Chen Z. A robust system for production of minicircle DNA vectors. 2010. Nature Biotech 28, 1287). The vector and the *E. coli* needed to produce the minicircle are commercially available from System Biosciences (SBI), Mountain View, Calif. (systembio.com), and are currently used by us.

The present invention of insulin expression constructs conforms to the generally accepted and proven placement scheme of various elements in relation to each other. Thus, the gene expression constructs of the present invention are comprised of AFP enhancer—conditional inducer-promoter-intron 1-gene-intron 2—termination/5' UTR. In our Examples, the GIREs are the conditional inducers and there is a translational enhancer inserted after the HGH intron and before the modified insulin gene. After the insulin gene, the second intron for efficient mRNA processing is from albumin followed by the 3' UTR of albumin.

Figure 4:
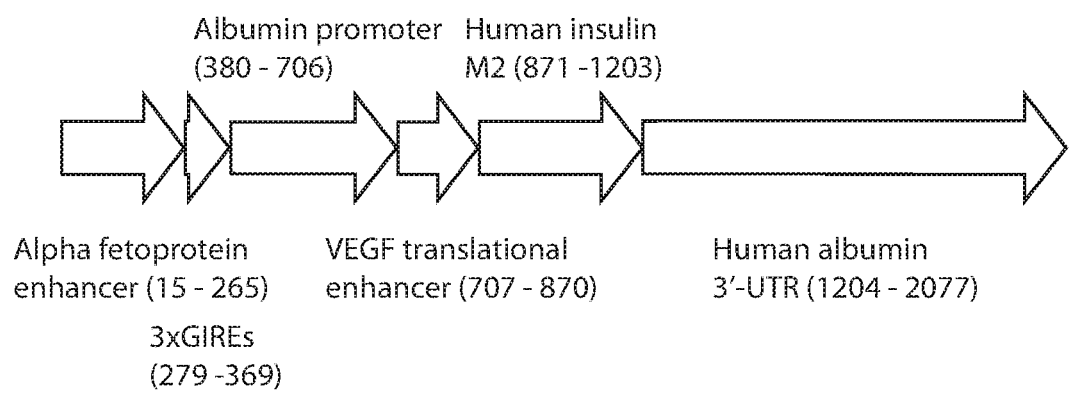
FIG. 4 is a diagram of the TA1 expression cassette.
Figure 5:
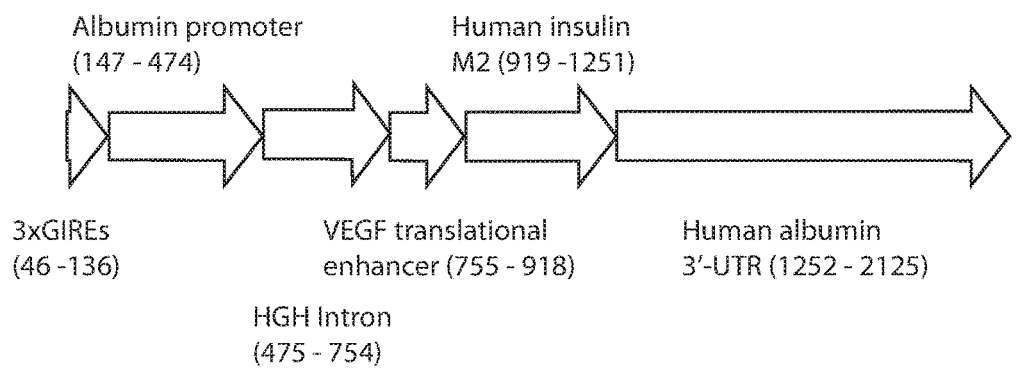
FIG. 5 is a diagram of the TA4 expression cassette.
Figure 10:
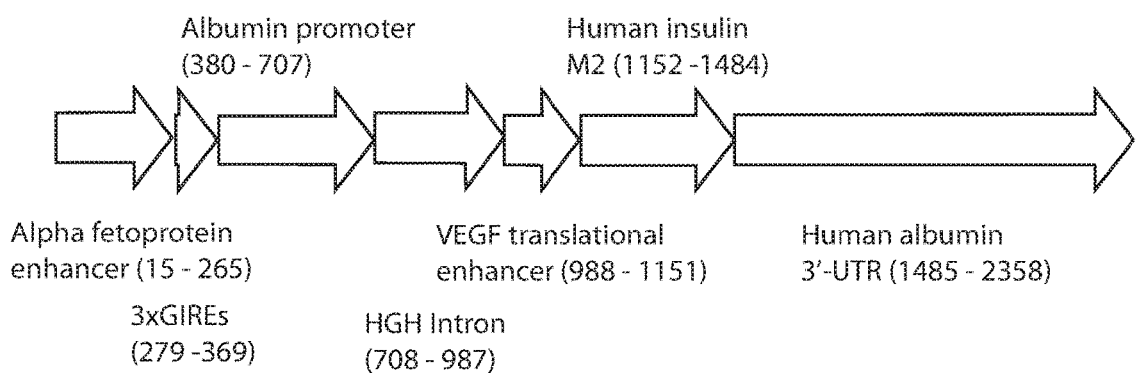
FIG. 10 is a diagram of the TA2 expression cassette.

FIGS. 4, 5 and 10 disclose preferred placement of elements in gene constructs of the present invention.

Method of the Present Invention

In one aspect, the present invention is a method of controlling blood glucose levels in a mammalian patient (preferably a human or non-human mammal), comprising the steps of treating a mammal with hepatocytes that have been modified with a first, second or third vector, as described above. The first vector comprises promoter enhancer, glucose inducible regulatory elements, a liver-specific promoter, a gene encoding insulin with modified peptidase site and an albumin 3' UTR and lacks an HGH intron. The second vector comprises an HGH intron, glucose inducible regulatory elements, a liver-specific promoter, a gene encoding insulin with modified peptidase site and the albumin 3' UTR and lacks promoter enhancer. The third vector comprises an HGH intron, glucose inducible regulatory elements, a liver-specific promoter, a gene encoding insulin with modified peptidase site, the albumin 3' UTR and promoter enhancer.

One would observe the mammal's blood glucose and insulin levels after vector treatment and note that the mammal's blood glucose or insulin levels are controlled and normal.

Figure 9:
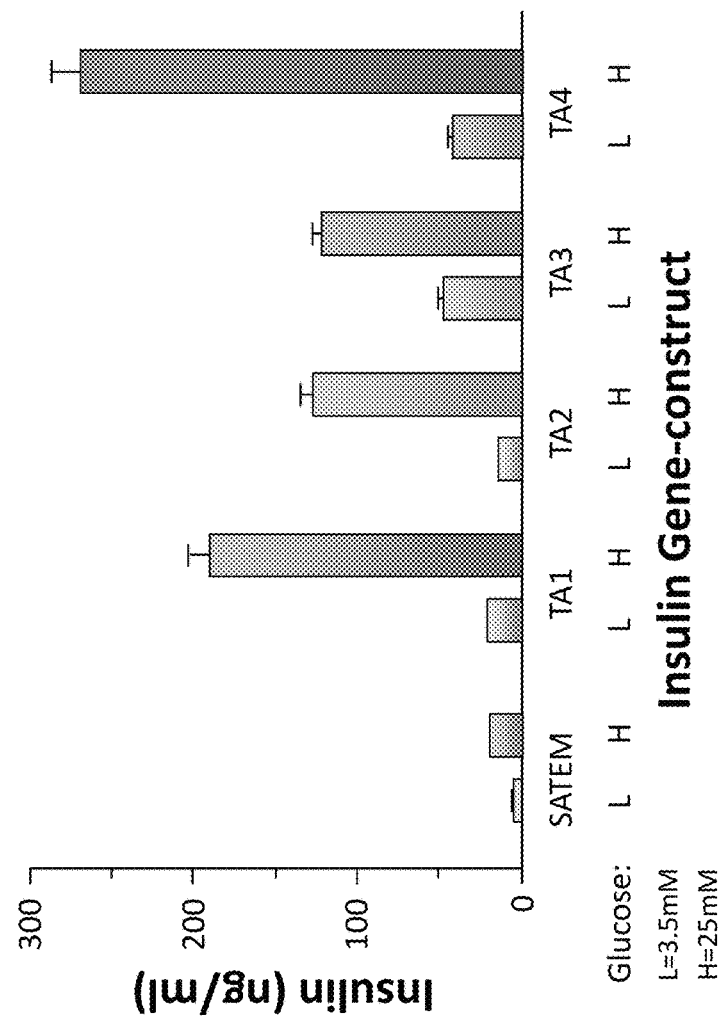
FIG. 9 is a bar chart comparing ex vivo insulin production in hepatocytes treated with various insulin gene constructs.

To test our insulin expression constructs ex vivo in hepatocytes, TA1, TA2 and TA4 insulin constructs were cloned in adenovirus vector, as described earlier (Alam T, Sollinger H W. Glucose-regulated insulin production in hepatocytes. Transplantation 2002; 74:1781.) Freshly isolated normal rat hepatocytes were plated on collagen coated cell culture plates and transfected with adenovirus containing the insulin gene construct. These cells were then exposed to low (3.5 mM), normal (5.6 mM) and high (27.5 mM) concentrations of glucose. Aliquots of medium were drawn at various time intervals and insulin present in the culture medium was quantitated by ELISA. Results showed that hepatocytes transfected with each insulin construct produced insulin in a glucose concentration dependent manner (FIG. 9). At the high concentration of glucose, the amount of insulin production was 4-10× higher than at the low concentration of glucose.

By "controlled," we mean that the method of the present invention is preferably characterized by tight control of glucose regulation. The tight control refers to the empirical observation of glucose regulation itself. In non-diabetic individuals, the blood glucose returns to normal at 2 hr post meal. Before the present invention, one would have anticipated that following the correction of hyperglycemia in a mammal in response to elevation in blood glucose levels, the preformed insulin mRNA would remain for a while and continue producing insulin. Depending on how long such a condition persists, one would expect that the mammal would then become hypoglycemic. However, our results showed that the insulin levels in serum increased soon after the increase in blood glucose levels, as we had anticipated, but the insulin levels did not stay high for too long and followed the blood glucose level curve with a delay of about 15-30 min (See FIG. 8).

Typically, the present invention provides that insulin levels will stay within 0.5 µU-100 µU/ml. (This is comparable to the maximum amount of insulin that is released from normal islets under hyperglycemic challenge of approximately 100 µU/ml.).

Typically, blood glucose concentration will stay within 80-150 mg/dl after treatment. The high end relates to a temporary rise soon after having a meal. If glucose concentration does rise above 150, the level does not stay at that level for beyond a short period (30-60 min).

Poorly controlled diabetes causes hyperlipidemia and the severity of hyperlipidemia is dependent on the degree of hyperglycemia. Liver function tests are performed for two reasons. Severe diabetes is associated with a degree of systemic inflammatory responses, including elevation in serum levels of some liver enzymes. Our data provide evidence that following insulin gene therapy, a correction in serum levels of liver enzymes is apparent. Secondly, the hydrodynamic deliver procedure is known to cause a transient stress to liver but this damage is short-lived. Our data support these findings and assert that there is no long-term risk associated with gene-therapy in the context of liver function. In fact, the therapy normalizes the liver function, as evidenced by the albumin production.

In one embodiment of the present invention, the lipid and/or liver enzyme profile of the treated animal is corrected. In one embodiment of the present invention, the animal will have a lipid/enzymes panel wherein the plasma lipid or liver enzymes concentration is equivalent to or less than a normal control. By "normal control" we mean an animal who is not diabetic. By "lipid/enzymes panel" we mean either a plasma triglycerides measurement, an alanine transaminase (AST), an aspartate transaminase (ALT) or plasma albumin measurement. In another embodiment of the invention, we would expect to see a drop in cholesterol (mg/dl) of at least 20% compared to a diabetic control. Based on a conservative estimate, approximately 1 week may be sufficient for a substantial correction or normalization of hyperlipidemia.

The method of the present invention involves the treatment of a mammal, preferably a human patient or non-human mammal, with the vectors of the present invention.

Introduction of our insulin expression constructs into liver cells can be achieved either in vivo or ex vivo. In the first method, the gene construct will be introduced either using a minicircle DNA by hydrodynamic method described herein, injecting the condensed minicircle DNA nanoparticles as such, or after coating nanoparticles with compounds that are known to target liver cells. Alternatively, liver cells will be harvested from the patient through a biopsy, expanded in cell culture, and transfected with a construct of the present invention using minicircle or safe viral vectors such as adeno-associated virus (AAV) (already used in many clinical trials).

The transfected cells will be tested for their ability to produce insulin and modulate the quantity of production of insulin in response to changes in concentrations of glucose. Appropriate number of cells to provide necessary amount of insulin (assisted with information from ex vivo measurements) will be transplanted into the liver of the mammal via radiological and ultrasound guidance. The ex vivo method allows for lower vector load as well as for targeted delivery of gene.

Incorporating scaffold/matrix-attachment regions (S/MARs) that serve as constitutively active anchors for the nuclear scaffold (Wong S P et al. Gene Ther. 2011; 18(1): 82-7; Heng H H et al. J Cell Sci. 2004; 117(Pt 7):999-1008; Lufino M M et al., Nucleic Acids Res. 2007; 35(15):e98. PMCID: 1976449) will likely increase the survival of TA1minicircle (TA1m)-containing S/MARs (TA1m-S/MAR) or other minicircles due to the association of SARs with the nuclear scaffold and may also reduce gene silencing (Wong S P et al. Gene Ther. 2011; 18(1):82-7).

The Examples below describe the delivery of DNA into rat liver by hydrodynamic procedures (Zhang G. et al., Methods Mol Biol 245:251-264, 2004; Zhang G. et al., Hum Gene Ther 8:1763-1772, 1997). The delivery of the DNA into mammalian liver will typically not be by the hydrodynamic method described in the Examples. Other alternatives, such as nano-particles of condensed DNA that do not require a large volume and high pressure, will be employed. In a preferred embodiment, suitable glucose regulation will last at least 2-4 weeks after treatment with the constructs.

Hydrodynamic venous delivery of naked plasmid DNA has led to successful gene uptake and transduction of liver cells (Sebestyen M G et al. Hum Gene Ther. 2007; 18(3): 269-85. PMCID: 2268901; Wooddell C I et al. J Gene Med. 2008; 10(5):551-63; Wooddell C I et al. Hum Gene Ther. 2011; 22(7):889-903. PMCID: 3135275). This method relies on a rapid, high-volume intravenous injection (~10% of body weight). However, with hydrodynamic venous delivery, much of the DNA is absorbed in the venous system, particularly the lungs, prior to its delivery to the liver. As an alternative, one may inject the vectors into the arterial system, such as the femoral artery, which has a systolic blood pressure of approximately 120 mm/Hg. The remaining vector will reach the liver via the portal vein at 10-12 cm·H$_2$O. (Blood pressure is usually presented in mm of Mercury (mm/Hg). Venous blood pressure is lower and sometimes a unit based on cm of water (cm/H$_2$O) is used.) Overall, intra-arterial injection should greatly enhance TA1m constructs uptake compared to hydrodynamic venous delivery.

Injection into the femoral artery should dramatically increase vector liver uptake and transduction of hepatocytes. We expect that treated animals will maintain normoglycemia for more than 1 month, even when fed ad libitum.

EXAMPLES

Example 1

Generation of Constructs

Human insulin based gene constructs containing various elements to modulate expression were generated with the aim of producing biologically active insulin in response to changes in glucose levels.

Four insulin constructs designated TA1, TA2, TA3, and TA4 contain various elements in order shown below:

| | AFP-Enhancer | 3GIREs | Alb-Promoter | HGH-intron | Human Insulin | Alb 3'-UTR |
|---|---|---|---|---|---|---|
| TA1 | Y | Y | Y | N | Y | Y |
| TA2 | Y | Y | Y | Y | Y | Y |
| TA3 | N | Y | Y | N | Y | Y |
| TA4 | N | Y | Y | Y | Y | Y |

AFP-Enhancer: Alphafetoprotein enhancer was used from Mirus vector pMIR0375.
3GIREs: 3 units of glucose inducible regulatory elements are connected in tandem; the sequences are based on S14. S14 is a glucose responsive transcriptional enhancer. The elements responsible for glucose-dependent transcriptional enhancement have been identified in published work: Shih H, Towle HC. Definition of the carbohydrate response element of the rat S14 gene: Context of the CACGTG motif determines the specificity of carbohydrate regulation. J Biol Chem 1994; 269: 9380.
Alb-Promoter: Albumin promoter (Albumin promoter was amplified by PCR from rat genomic DNA, as described in U.S. Pat. No. 6,352,857, U.S. Pat. No. 6,933,133, U.S. Pat. No. 7,425,443 and the following publication: Alam T, Sollinger HW. Glucose-regulated insulin production in hepatocytes. Transplantation 2002; 74: 1781)
HGH-intron: Human growth hormone intron was amplified by PCR from a commercially available plasmid pAAV-LacZ (Stratagene).
Human Insulin: Human insulin cDNA sequence was modified at B-C and C-A junction for furin cleavage compatibility so that liver cells are able to process preproinsulin to functional insulin.
Alb 3'-UTR: Albumin 3'-untranslated region was used from Mirus vector pMIR0375. It can also be amplified by PCR using reverse transcribed mRNA from liver.

Insulin expression constructs described above were incorporated into replication-defective adenovirus for transient expression for initial testing purposes. Insulin expression in rat hepatocytes, ex vivo, was glucose responsive and each construct yielded significantly higher amount of insulin (4-12 fold improvement over the previously described constructs), Alam & Sollinger, Transplantation. 2002 Dec. 27; 74(12):1781-7.

TA2 and TA3 were also tested in ex vivo insulin production. (See FIG. 9).

Initially we incorporated TA1 in an adenovirus vector to test its ability to control hyperglycemia in rats that were rendered diabetic by streptozotocin (STZ) treatment. Results showed that such a treatment fully corrected fasting hyperglycemia, restored the weight loss caused by diabetes to normal rate of weight gain and significantly reduced postprandial hyperglycemia.

The adenovirus vectors containing TA1-TA4 were tested individually for their ability to correct diabetic hyperglycemia in STZ-rats. Results showed a full correction of fasting hyperglycemia and a partial correction of postprandial hyperglycemia. The benefit of a single gene therapy treatment on overall metabolism and preventing body weight loss lasted well beyond the time of full correction of fasting hyperglycemia. During the period of full correction of fasting hyperglycemia, the rate of weight gain in diabetic rats treated with our insulin gene constructs was indistinguishable from the normal controls.

To improve efficacy of gene therapy through better gene expression by increasing levels and duration of insulin expression, minicircles of DNA containing only the gene expression constructs were produced. All of the above insulin gene expression constructs were cloned into a plasmid vector p2ϕC31 as previously described (Chen et al., 2003, Mol Ther, 8, 495-500; Chen et al., 2005, Human Gene Ther, 16, 126-131). This published method of Chen et al. was substantially modified to improve purity of minicircle DNA as described below.

Encouraged by results from transient expression afforded by adenovirus vector, we generated a plasmid vector, known as "minicircle DNA," that is virtually devoid of all DNA sequences that are unrelated to expression of insulin. TA1 minicircle was introduced into the livers of rats via an established hydrodynamic procedure (Zhang G. et al., Methods Mol Biol 245:251-264, 2004; Zhang G. et al., Hum Gene Ther 8:1763-1772, 1997). Results obtained from STZ-diabetic rats treated with TA1 minicircle DNA show a full correction of hyperglycemia among ad lib fed animals (FIG. 1) in addition to restoration of rate of weight gain to normal (FIG. 2) and correction of fasting hyperglycemia.

Figure 8:
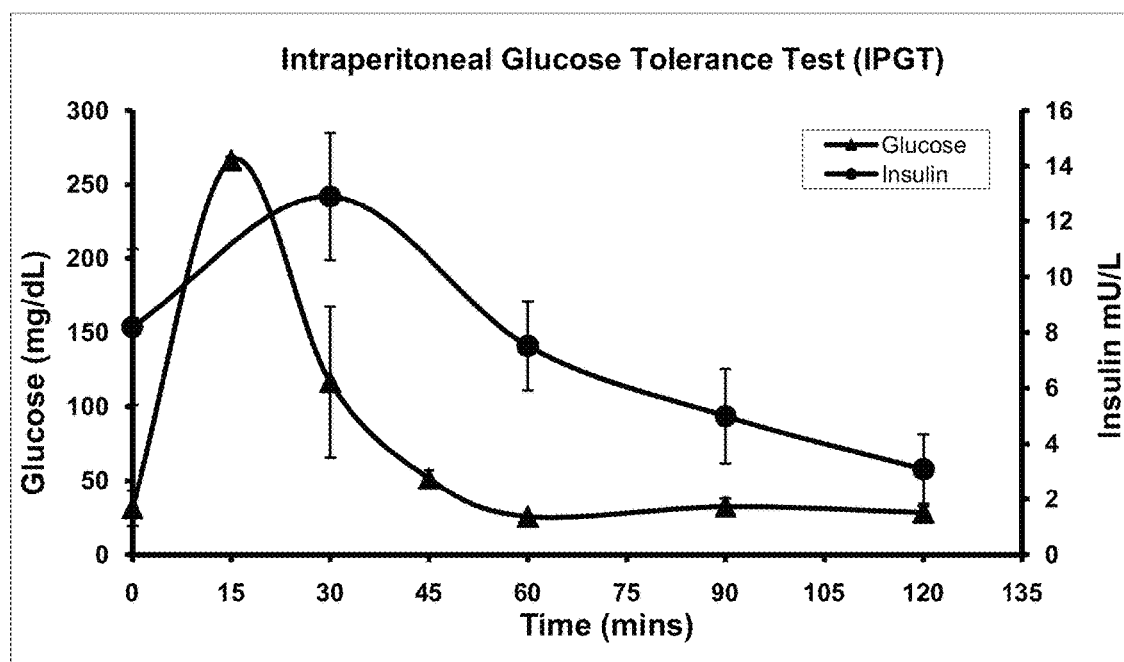
FIG. 8 is a diagram of glucose levels versus time versus insulin levels during an intraperitoneal glucose tolerance test of TA1-treated diabetic rats.

The TA1-minicircle-treated diabetic rats were subjected to a glucose tolerance test by intraperitoneal injections of 4 gm/kg glucose. Results from these experiments bore a marked similarity to observations from normal control rats. The peak of elevated blood glucose levels appeared at 15 min post injection and hyperglycemia dissipated in about 60 min (FIG. 8). The time to correct hyperglycemia induced by 4 gm/kg glucose IP injection is similar to normal animals. An increased insulin output in response to elevated levels of glucose closely follows the rise in glucose levels and insulin production declines as the level of glucose progressively reduces.

To confirm that insulin production was glucose-dependent, we measured human insulin levels in plasma at 30 min time intervals and found that the human insulin levels peaked at 30 min and declined relatively quickly, essentially following the blood glucose profile with a 15 min delay. Thus, there was an approximately 15 min lag between the profiles of blood glucose and insulin levels.

Given the nature of glucose-induced transcription of insulin mRNA that gives rise to circulating insulin, after achieving euglycemia, continued presence of insulin mRNA could have caused a sustained secretion of high levels of insulin until the mRNA was degraded. Reduction in insulin levels in only ~60 min to the levels observed in fasting animals prior to glucose injections, is an unexpected, albeit very desirable, result.

Modifications to the published minicircle DNA production method were useful and necessary to obtain pure minicircle DNA that was free of detectable unprocessed or partially processed minicircle DNA. These modifications involved elimination of a 2 hr incubation step, claimed to be necessary for in vivo digestion of the DNA circle that consists of the unneeded sequences from the parental plasmid that were eliminated from the minicircle containing the gene of interest. In practice, this step was only partially effective.

In our procedure, elimination of this 2 hr incubation step caused no perceptible change in quality or quantity of recovered DNA and the final product was comprised of a mixture of minicircle DNA and the parental unprocessed plasmid DNA as well as partially processed plasmid DNA. The mixture of DNA thus produced was treated, ex vivo, with a restriction enzyme that could cut the parental plasmid but not the minicircle DNA containing our insulin gene constructs. The product of this reaction was purified by CsCl equilibrium density gradient to separate the circular DNA from linear DNA.

Figure 2:
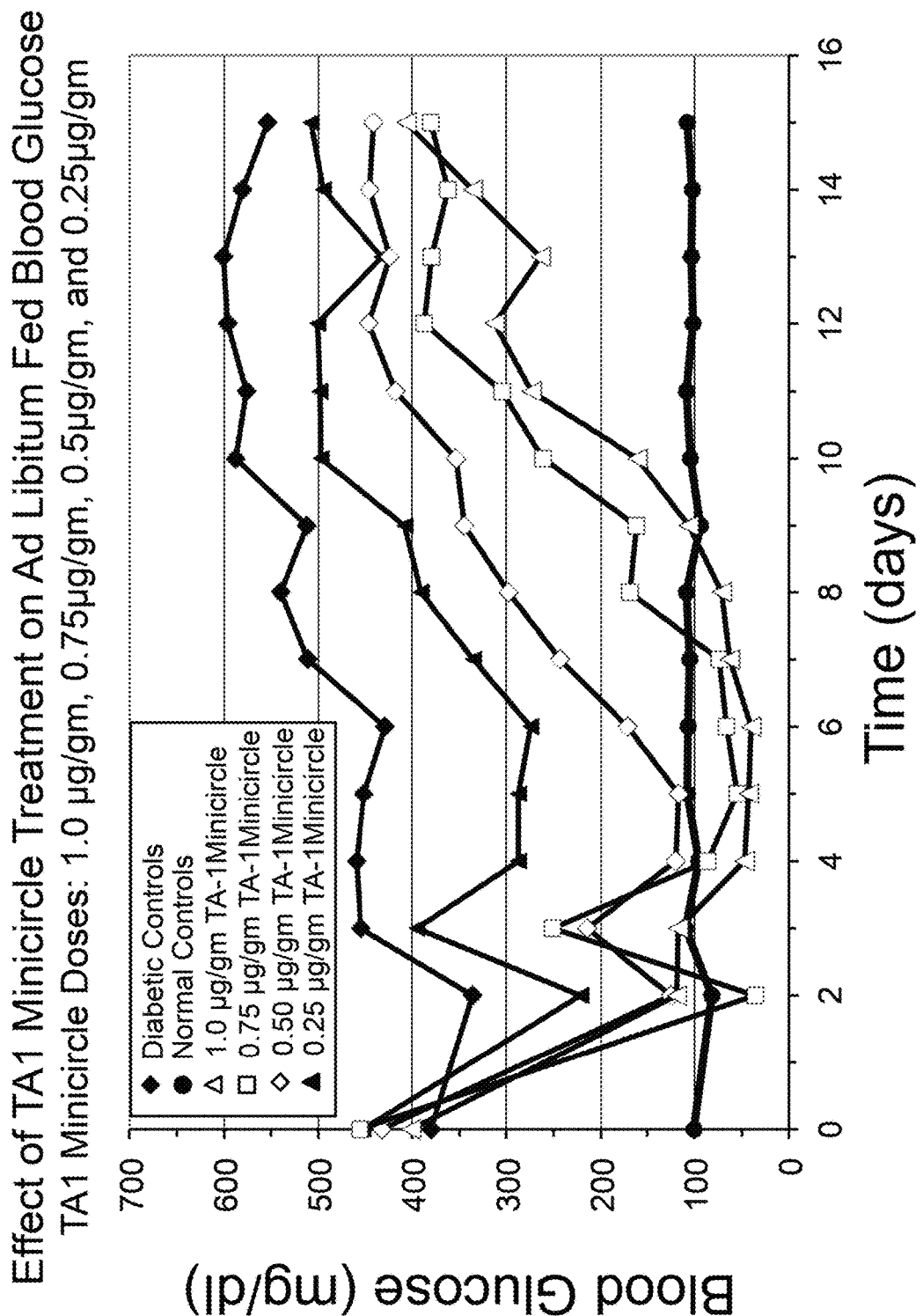
FIG. 2 is a graph comparing postprandial blood glucose levels versus time for TA-1 minicircle DNA treated STZ-treated diabetic rats.
Figure 3:
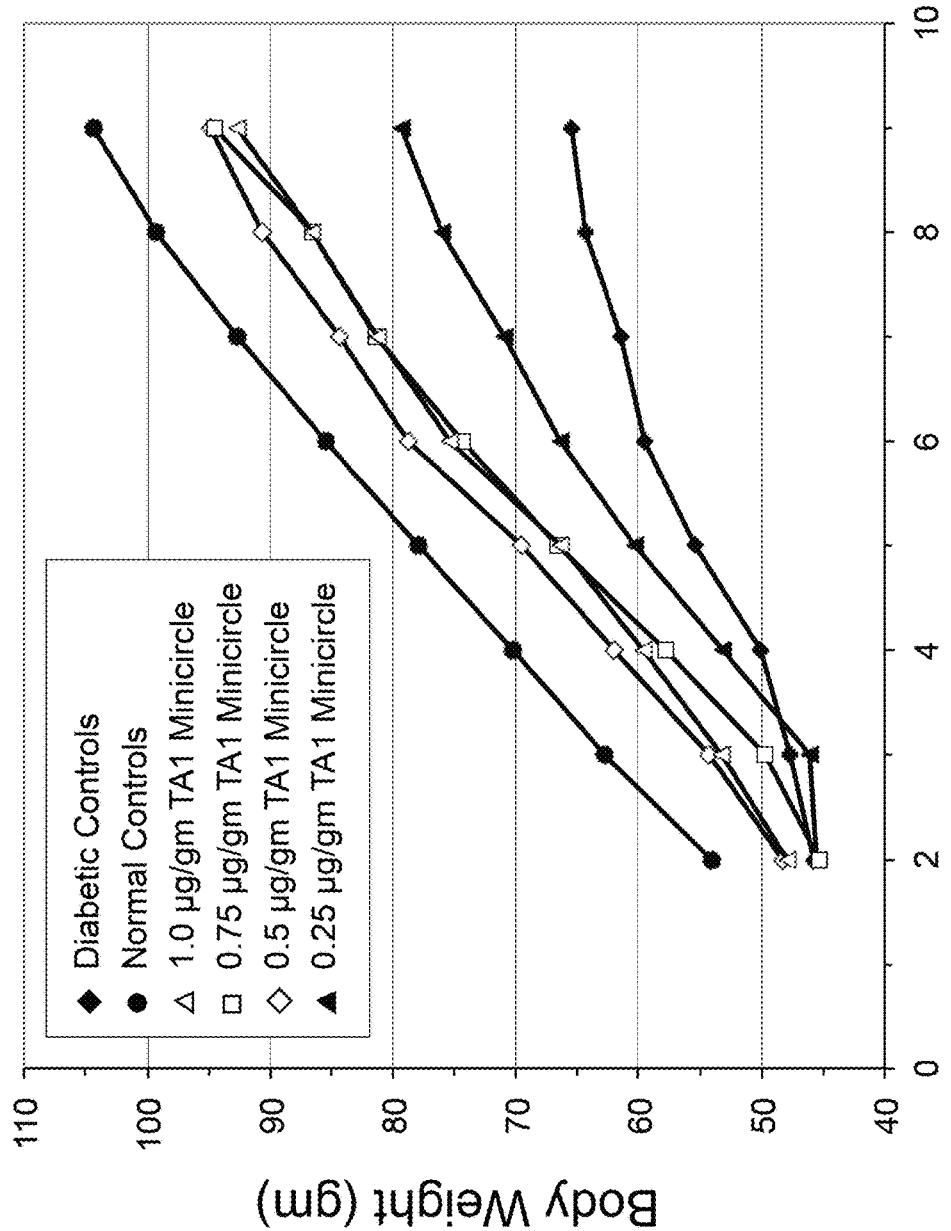
FIG. 3 is a graph comparing fasting body weight versus time in TA-1 minicircle DNA treated STZ-treated diabetic rats.

The TA1 insulin minicircle DNA was tested for its ability to correct diabetic hyperglycemia in STZ-treated diabetic rats. Groups of rats were rendered diabetic by intravenous streptozotocin injections (100 mg/kg). The TA1 insulin minicircle DNA was injected via tail vein into diabetic rats according to a previously published method (hydrodynamic delivery method described by J. Wolff group, Zhang G. et al., *Methods Mol Biol* 245:251-264, 2004; Zhang G. et al., *Hum Gene Ther* 8:1763-1772, 1997). Four groups of diabetic rats were injected with indicated amounts of TA1 minicircle DNA (1.0 µg, 0.75 µg, 0.5 µg, and 0.025 µg per gm body weight). Results are shown in FIGS. 1, 2, and 3.

This is the first time we have been able to fully correct blood glucose levels in diabetic rats fed ad libitum (FIG. 2) by insulin gene therapy. This treatment fully restored rate of weight gain in diabetic rats (FIG. 3).

Example 2

Creation of Adenovirus Constructs

Figure 12:
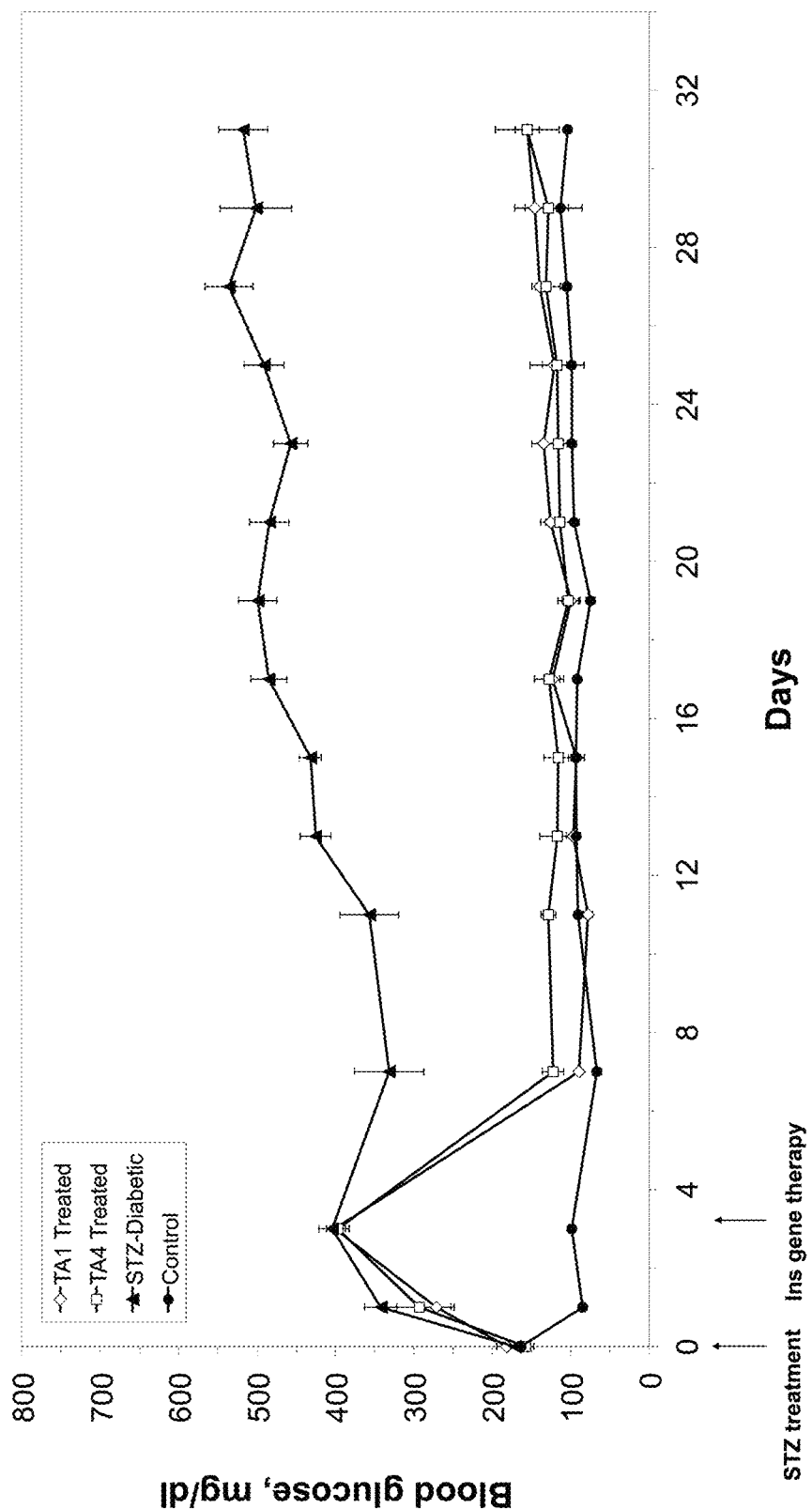
FIG. 12 is a diagram of blood glucose versus days in rats, fasted overnight and treated with TA1 and TA4 constructs.

Referring to FIG. 12, insulin constructs TA1 and TA4 were created in adenovirus and equal plaque forming units injected into rat livers, as indicated. TA1 and TA4 were used under identical conditions. Both were able to fully correct fasting hyperglycemia, as shown in FIG. 12. However, the vectors did not fully correct blood glucose levels in rats fed ad libitum.

Figure 13:
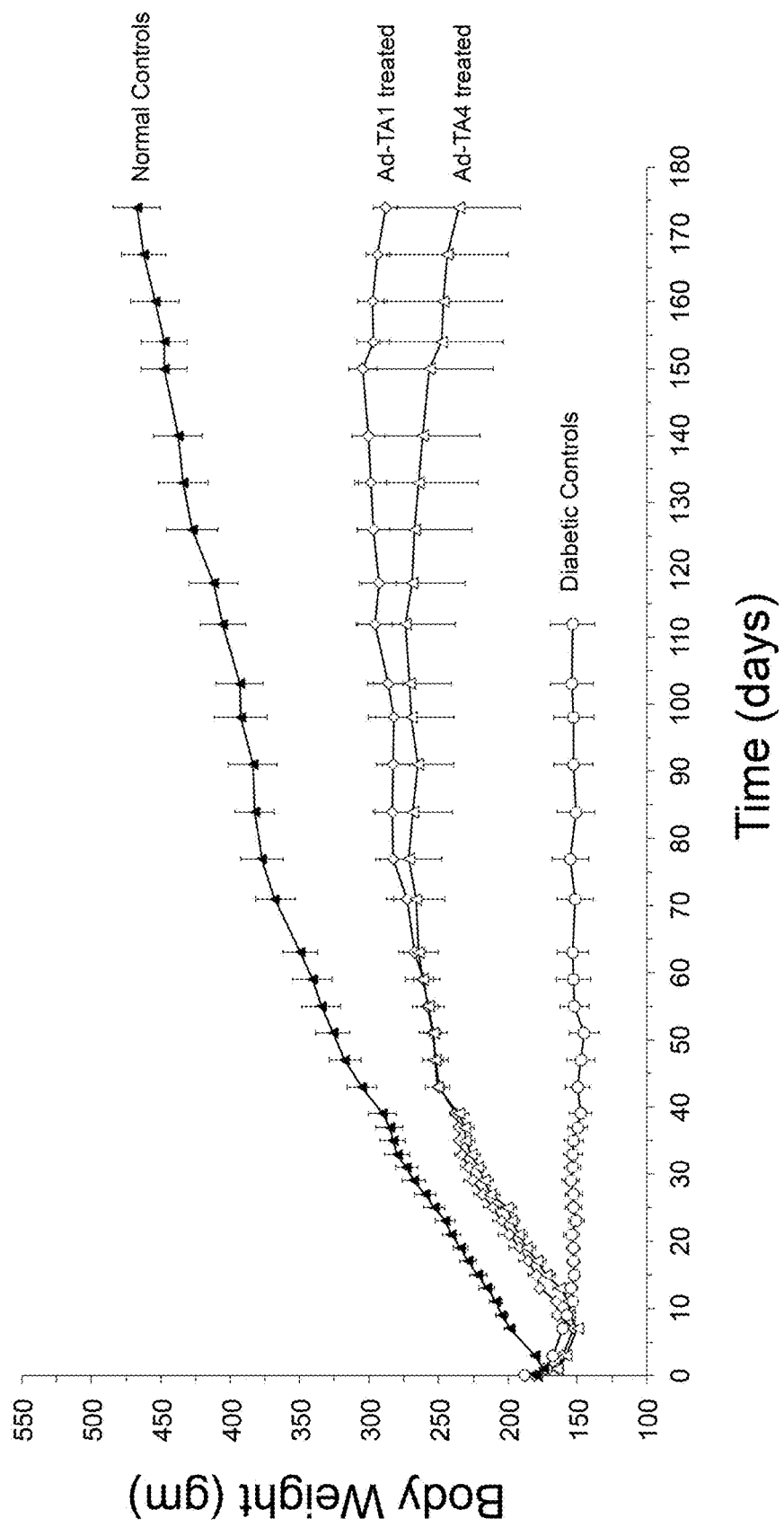
FIG. 13 is a diagram of body weight versus days in rats treated with TA1 gene construct.

Referring to FIG. 13, TA1 in adenovirus was injected into rat livers as indicated. Note that the TA1 treated rats regained the weight initially lost due to diabetes and maintained a higher weight than the STZ diabetic rats.

Figure 14:
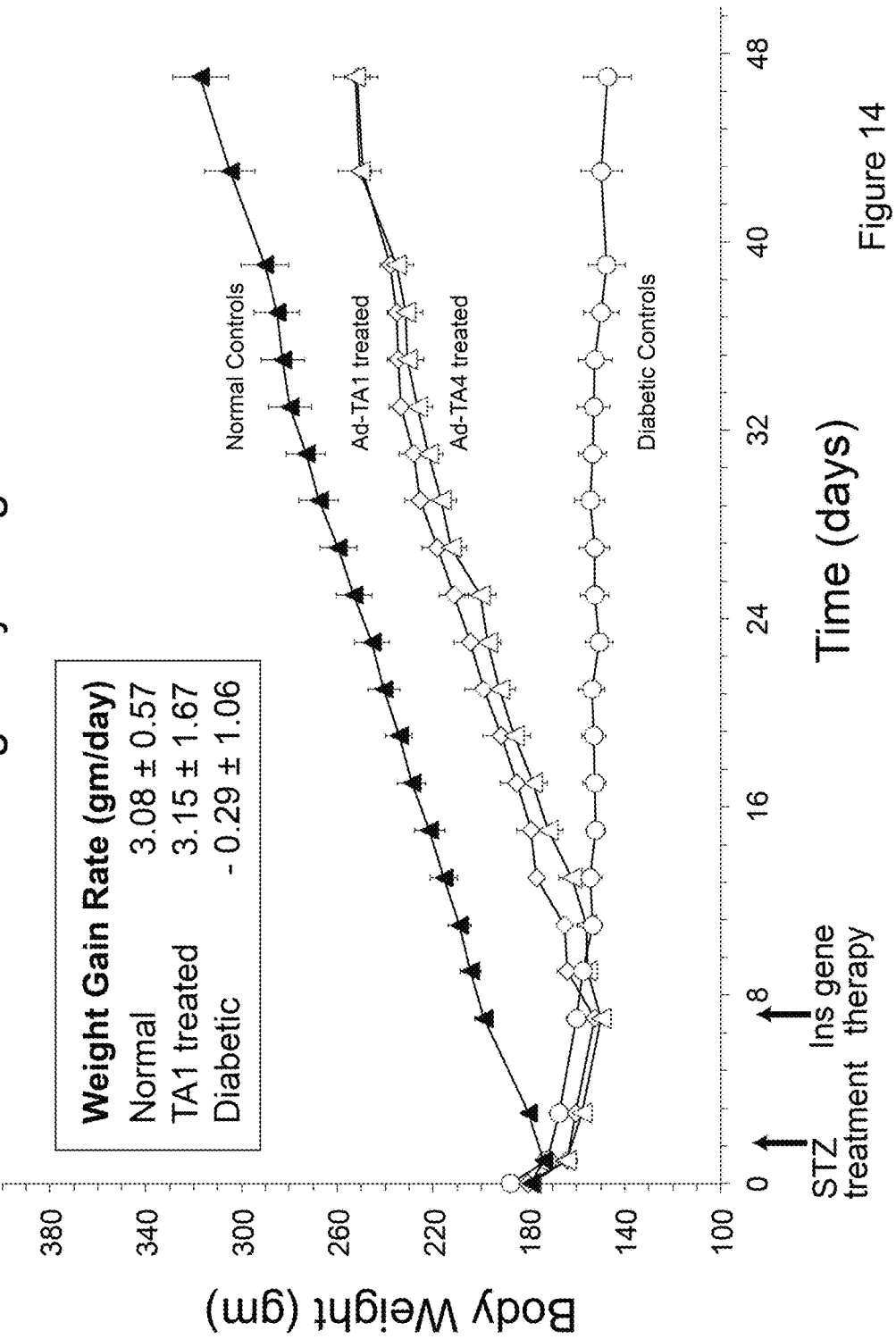
FIG. 14 is a graph of body weight versus days on rats treated with TA1 and TA4 gene construct.

Referring to FIG. 14, TA1 or TA4 in adenovirus was injected into livers of diabetic rat groups, as indicated. Note that both TA1 treated and TA4 treated rats had maintained higher body weight than STZ diabetic rats. FIG. 14 shows a subset of data points from FIG. 13, representing 0-48 days. The information on rate of weight gain in various groups of rats (shown in the inset box on the top left corner) is derived from data obtained 24 days post treatment (d8-d31). The rate of weight gain in diabetic rats treated with TA1 in adenovirus is equal to normal control rats, whereas the diabetic untreated rats experienced a net loss of weight on a daily basis. FIG. 13 has many more data points, and the early days occupy only a small portion of the area, and therefore the degree of correction in weight gain may be somewhat difficult to appreciate. FIG. 14 shows this aspect more clearly.

Example 3

Evaluation of Human Insulin in Serum of Diabetic Rats

Referring to FIG. 15, a comparison of human insulin in rat serum shows that animals treated with TA1 minicircle DNA produce larger amounts of insulin compared to other plasmid vectors (pTED110, TA1/pENTR). The plasmid pENTR contains an ampicillin resistance gene which has been replaced by a Kanamycin resistance gene in pTED110, and S/MAR has also been added to it; both have the TA1 insulin construct. The TA1 minicircle containing S/MAR produced the most insulin in vivo. The Ultrasensitive Human Insulin ELISA (Mercodia, Inc) has a detection limit of 0.15-20 mU/L, as advertised. The table in FIG. 15 shows the relative in vivo effectiveness of various vectors used for insulin gene therapy. All insulin vectors contained the TA1 expression cassette. pENTR is a commercial plasmid containing an ampicillin resistance gene. The pTED is our modified plasmid where we replaced the ampicillin resistance gene with kanamycin resistance gene to increase the in vivo survival of the vector in non-dividing cells.

We also added S/MAR to pTED110 to increase survival of vector in dividing cells and to some degree, increase the overall expression. The data are in agreement with our vector design expectations.

Finally, when extraneous sequences were eliminated and insulin gene constructs were used as minicircle DNA molecules, the expression levels of insulin were significantly increased, more so when S/MAR was included in the minicircle. In all four sets of experiments, the molar equivalence of TA1 was maintained at a constant level.

The table (FIG. 15) in conjunction with data obtained from adenovirus mediated transduction ex vivo (FIG. 9) and in vivo (FIG. 12 and FIG. 13, FIG. 14, and FIG. 17) provides the proof that the insulin expression cassettes are able to produce glucose-dependent insulin, as intended. However, the magnitude and longevity of insulin expression does depend on the vector employed to deliver the insulin expression cassette(s). We expect that these insulin expression cassettes will be readily adaptable to take advantage of new vectors developed to have better characteristics for gene therapy, such as ease of delivery, expression level, and longevity of expression Example 4

Second Treatment with TA1M

Figure 16:
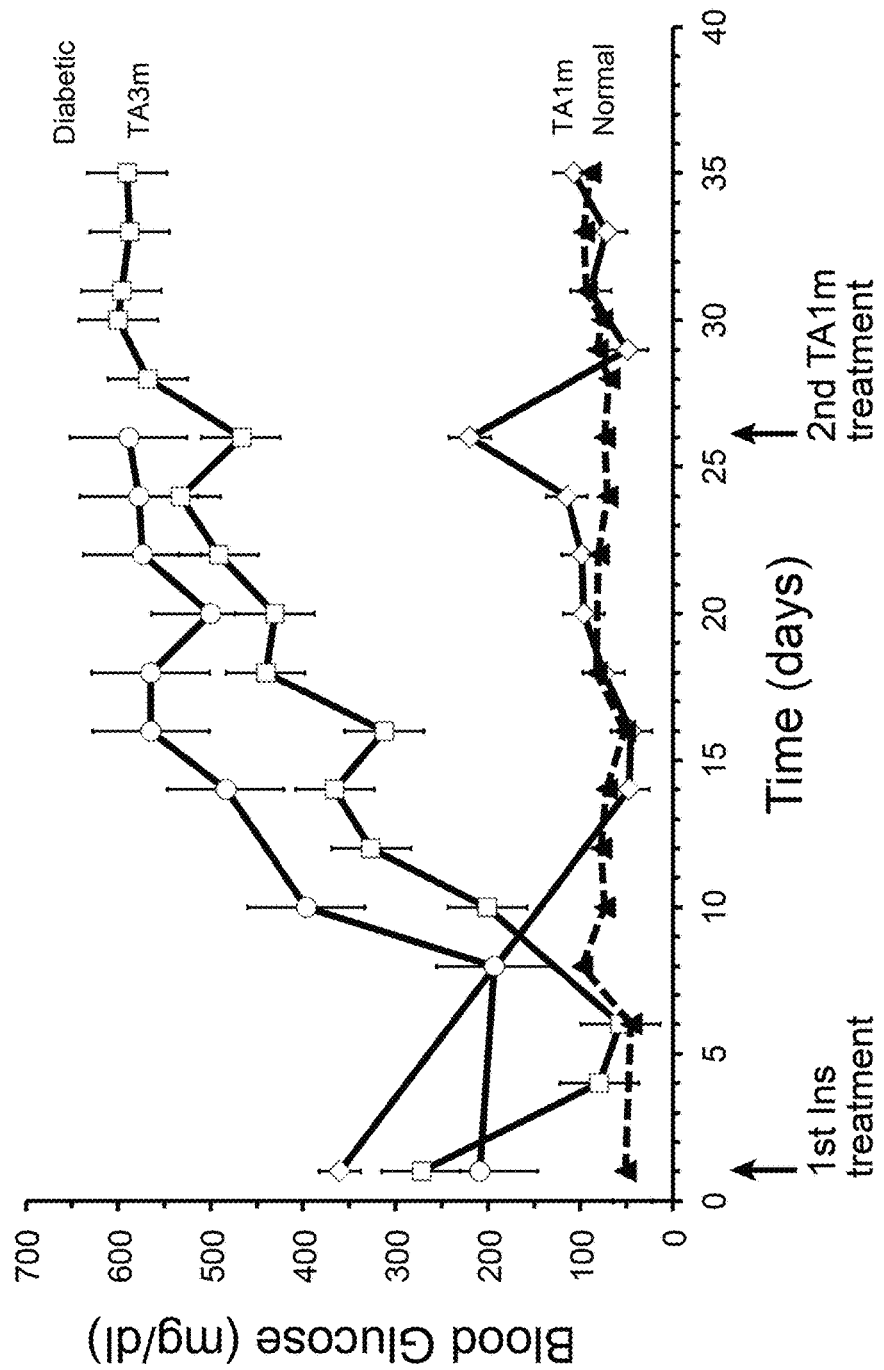
FIG. 16 is a graph of blood glucose levels versus time for rats experiencing a second treatment of TA1 minicircle DNA.

Referring to FIG. 16, a second treatment with TA1 minicircle DNA corrects the gradually elevating fasting blood glucose to normal level.

FIG. 1 discloses data that are relevant to the information presented in FIG. 16. As the information in two figures comes from different studies, individual data points are not identical, but the trend is the same. One should refer to the curve corresponding to use of 1.0 μg/gm TA1 minicircle DNA in FIG. 1 for comparison. FIG. 16 shows that it appears possible to correct hyperglycemia by a second treatment as the effect of the first treatment diminishes.

Example 5

Hepatocytes Derived from Human Stem Cells

Referring to FIG. 17, hepatocytes were derived from human embryonic stem (hES) cells and human adult induced pluripotent (iPS) cells as described in Si-Tayeb et al 2010. Hepatology 51(1):297-305:. PMCID: 2946078 and were transduced with TA1 in adenovirus, ex vivo. Three cell culture plates were kept in medium with low glucose (3.5 mM), and three plates were kept in high glucose (27.5 mM). Freshly prepared normal rat hepatocytes were treated similarly. Flasks containing stem cell derived hepatocytes were confluent with cells, whereas primary rat hepatocyte plates were ~60% confluent.

Results (FIG. 17) show a robust production of glucose-dependent insulin in embryonic and induced pluripotent-cell-derived hepatocytes.

Example 6

Examination of Rat Weight after Treatment with Minicircle Vectors

Figure 18:
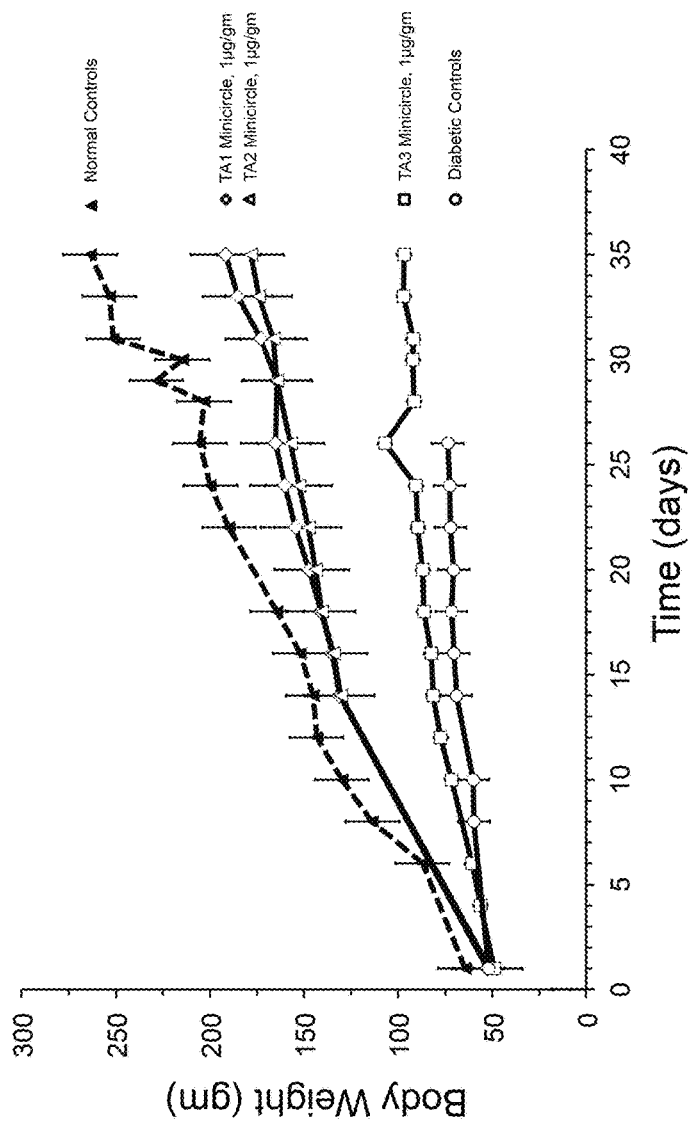
FIG. 18 is a graph of body weight versus days for diabetic rats treated with TA1M, TA2M and TA3M.

Referring to FIG. 18, groups of diabetic rats (minimum number of rats in a group=5) were injected with the indicated insulin minicircle DNA, TA1, TA2, or TA3, via tail veins. Fasting body weights (Mean±S.D) of rats are shown. Normalization in rate of weight gain is similar when TA1 m or TA2m was used, whereas TA3m was less effective.

Example 7

Evaluation of Lipid Profiles

Two groups of rats were rendered diabetic by intravenous streptozotocin treatment. One group of diabetic rats (n=5) was treated with 1 μg TA1 minicircle DNA/gm body weight of animal. The second group of diabetic rats was used as an untreated control. A third group of normal rats was included as age matched healthy controls. Blood was drawn from each experimental animal after 10 days, and plasma was analyzed for lipid contents and various markers of liver damage and hepatic function, as shown in the table below:

| Animal Groups | Triglycerides (mg/dl) | Cholesterol (mg/dl) | Aspartate Transaminase (U/L) | Alanine Transaminase (U/L) | Alkaline Posphatase (U/L) | Plasma Albumin (g/dl) |
|---|---|---|---|---|---|---|
| TA1m Treated | 53 ± 34 | 141 ± 15 | 302 ± 33 | 77 ± 40 | 210 ± 95 | 3.4 ± 0.2 |
| Diabetic | 704 ± 313 | 191 ± 36 | 617 ± 349 | 152 ± 75 | 423 ± 73 | 2.5 ± 0.2 |
| Normal Control | 100 ± 14 | 129 ± 6 | 504 ± 100 | 106 ± 16 | 172 ± 55 | 3.4 ± 0.1 |

TA1m treatment corrected all deficiencies caused by the uncontrolled diabetes. Thus, the levels of cholesterol and triglyceride in plasma of treated rats were reversed to normal levels. Likewise liver function markers showed an improvement and reduced levels of albumin in diabetic rats returned to normal.

We claim:

1. A method for obtaining glucose-regulated expression of insulin ex vivo in mammalian hepatocytes, wherein the method comprises delivering a first, second or third genetic vector for glucose-regulated synthesis of insulin into an isolated mammalian hepatocyte and wherein the insulin levels in the blood of the mammal stays within 0.5 uU-100 uU/ml and the blood glucose concentration of the mammal stays within 80-150 mg/dl for at least 10 days after transplant of the mammalian hepatocytes into a mammal, wherein the first vector comprises SEQ ID NO:1, wherein the second vector comprises SEQ ID NO:2, wherein the third vector comprises SEQ ID NO:3, and wherein glucose-regulated expression of insulin occurs.

2. The method of claim 1 additionally comprising the step of transplanting the hepatocytes back into a mammal.

3. The method of claim 1, wherein the genetic vector is delivered by exposing the cells to a virus infective for the cells, wherein the virus comprises the genetic construct, and whereby at least a portion of the cells are infected by the virus under suitable conditions and at a sufficient multiplicity.

4. The method of claim 1 wherein the mammal is human.

5. A vector suitable for controlling blood glucose levels in a mammal, wherein the vector comprises SEQ ID NO: 1;or wherein the vector comprises SEQ ID NO: 2;or wherein the vector comprises SEQ ID NO: 3.

6. A method of controlling blood glucose levels in a mammal, comprising the steps of:

treating a mammal with a first, second or third vector, wherein the first vector comprises SEQ ID NO:1; and wherein the second vector comprises SEQ ID NO:2; and wherein the third vector comprises SEQ ID NO:3; and observing the mammal's insulin levels, wherein the mammal's insulin levels are controlled by the glucose-regulated synthesis of insulin by the first or second or third vector, and wherein the blood glucose level in the mammal is under tight control by the vector after treatment.

7. The method of claim 1 wherein the vector is in a minicircle format.

8. The method of claim 6 wherein the vector is in a minicircle format.

9. The method of claim 6 wherein the mammal is human.

10. The method of claim 6 wherein the mammal's cholesterol level decreases after treatment.

11. The method of claim 6 wherein the mammal's triglyceride level decreases after treatment.

12. The method of claim 6 wherein the mammal is a cat.

13. The method of claim 6 wherein the mammal is a dog.

14. The method of claim 6 wherein the mammal is selected for the group consisting of hamsters, gerbils, rats, mice, rabbits, guinea pigs, chinchillas and ferrets.

15. The method of claim 6 wherein the mammal is a non-human mammal.

16. The method of claim 6 wherein the patient has a decrease in the plasma level of a compound selected from the group of alanine transaminase (AST), aspartate transaminase(ALT), and alkaline phosphatase after treatment.

17. The method of claim 6 wherein after treatment with the vector the mammal stays within 80-150 mg/dl blood glucose for at least 10 days after treatment.

18. The method of claim 6 wherein insulin levels in the blood of the mammal stay within 0.5 uU-100 uU/ml for at least 10 days after treatment with the vector.

19. The method of claim 6 wherein the mammal has at least a 24 fold increase in insulin production after treatment.

20. The method of claim 6 wherein the symptoms of diabetes are relieved after treatment with the vector.

21. The method of claim 6 wherein the blood glucose level in the mammal is under tight control by the vector for 2-4 weeks.

* * * * *